United States Patent
Wang et al.

(10) Patent No.: US 11,912,761 B2
(45) Date of Patent: Feb. 27, 2024

(54) IL-1β NEUTRALIZING HUMAN MONOCLONAL ANTIBODIES

(71) Applicant: Agency for Science, Technology and Research, Singapore (SG)

(72) Inventors: Cheng-I Wang, Singapore (SG); Angeline Goh, Singapore (SG); Siok Ping Yeo, Singapore (SG); Alessandra Rosa Mortellaro, Singapore (SG); Subhra Kumar Biswas, Singapore (SG); Florent Ginhoux, Singapore (SG); Pingyu Zhong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 458 days.

(21) Appl. No.: 17/150,689

(22) Filed: Jan. 15, 2021

(65) Prior Publication Data

US 2021/0155685 A1 May 27, 2021

Related U.S. Application Data

(62) Division of application No. 16/192,537, filed on Nov. 15, 2018, now Pat. No. 10,919,962, which is a division of application No. 14/378,442, filed as application No. PCT/SG2013/000057 on Feb. 13, 2013, now Pat. No. 10,167,335.

(30) Foreign Application Priority Data

Feb. 13, 2012 (SG) ............................... 201201007-0

(51) Int. Cl.
  *A61K 39/395* (2006.01)
  *C07K 16/24* (2006.01)
  *A61K 39/00* (2006.01)

(52) U.S. Cl.
  CPC ........ *C07K 16/245* (2013.01); *A61K 39/3955* (2013.01); *A61K 2039/505* (2013.01); *C07K 2317/10* (2013.01); *C07K 2317/55* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
  CPC ................................................ A61K 39/3955
  See application file for complete search history.

(56) References Cited

U.S. PATENT DOCUMENTS

| | | |
|---|---|---|
| 6,168,791 B1 | 1/2001 | Larsen et al. |
| 6,632,927 B2 | 10/2003 | Adair et al. |
| 6,818,418 B1 | 11/2004 | Lipovsek et al. |
| 7,250,297 B1 | 7/2007 | Beste et al. |
| 7,531,166 B2 | 5/2009 | Masat et al. |
| 7,541,033 B2 | 6/2009 | Dickinson et al. |
| 7,566,772 B2 | 7/2009 | Green et al. |
| 7,582,742 B2 | 9/2009 | Masat et al. |
| 7,608,694 B2 | 10/2009 | Lawson et al. |
| 7,695,717 B2 | 4/2010 | Masat et al. |
| 7,714,120 B2 | 5/2010 | Dickinson et al. |
| 7,744,865 B2 | 6/2010 | Masat et al. |
| 7,744,866 B2 | 6/2010 | Masat et al. |
| 7,829,093 B2 | 11/2010 | Masat et al. |
| 7,829,094 B2 | 11/2010 | Masat et al. |
| 7,943,121 B2 | 5/2011 | Masat et al. |
| 7,964,193 B2 | 6/2011 | Green et al. |
| 7,988,968 B2 | 8/2011 | Masat et al. |
| 8,377,442 B2 | 2/2013 | Masat et al. |
| 8,398,966 B2 | 3/2013 | Wu et al. |
| 8,465,744 B2 | 6/2013 | Lawson et al. |
| 9,206,252 B2 | 12/2015 | Masat et al. |
| 10,167,335 B2 | 1/2019 | Wang et al. |
| 10,919,962 B2 | 2/2021 | Wang et al. |
| 2003/0007972 A1 | 1/2003 | Tobinick |
| 2004/0132028 A1 | 7/2004 | Stumpp et al. |
| 2007/0224633 A1 | 9/2007 | Skerra et al. |
| 2008/0139791 A1 | 6/2008 | Lipovsek et al. |
| 2011/0223165 A1 | 9/2011 | Ng et al. |
| 2015/0037248 A1 | 2/2015 | Wang et al. |
| 2019/0048072 A1 | 2/2019 | Ligueros-Saylan et al. |
| 2019/0144535 A1 | 5/2019 | Wang et al. |
| 2021/0024627 A1 | 1/2021 | Wang et al. |
| 2021/0127228 A1 | 4/2021 | Baarman et al. |
| 2021/0155686 A1 | 5/2021 | Wang et al. |

FOREIGN PATENT DOCUMENTS

| | | |
|---|---|---|
| EP | 1248804 A2 | 10/2002 |
| EP | 1641818 | 4/2006 |
| JP | 2004506448 A | 3/2004 |
| JP | 2008543340 A | 12/2008 |
| WO | 2000029004 A1 | 5/2000 |
| WO | 0216436 A2 | 2/2002 |
| WO | 2005056764 A2 | 6/2005 |

(Continued)

OTHER PUBLICATIONS

Fiedler et al. Chapter 7—Non-Antibody Scaffolds from Handbook of Therapeutic Antibodies. pp. 467-499 (2007).
Holliger et al. "Diabodies": small bivalent and bispecific antibody fragments. PNAS USA 90(14):6444-6448 (1993).
Holliger et al.: Engineered antibody fragments and the rise of single domains. Nat. Biotechnol. 23(9):1126-36 (2005).
U.S. Appl. No. 14/378,442 Office Action dated Jan. 5, 2017.
U.S. Appl. No. 14/378,442 Office Action dated Jun. 28, 2017.
Ali et al., Transferrin trojan horses as a rational approach for the biological delivery of therapeutic peptide domains. J Biol Chem. Aug. 20, 1999;274(34):24066-73.
Amit et al., Three-dimensional structure of an antigen-antibody complex at 2.8 A resolution. Science. Aug. 15, 1986;233(4765):747-53. PubMed PMID: 2426778.

(Continued)

*Primary Examiner* — Prema M Mertz
(74) *Attorney, Agent, or Firm* — Wolf, Greenfield & Sacks, P.C.

(57) ABSTRACT

The present invention is directed to antigen binding proteins and in particular to IL-1β antigen binding proteins. The present invention further provides compositions comprising the antigen binding proteins, use of the antigen binding proteins and methods for production.

18 Claims, 18 Drawing Sheets

Specification includes a Sequence Listing.

(56) References Cited

FOREIGN PATENT DOCUMENTS

| WO | 2006081139 A2 | 8/2006 |
|---|---|---|
| WO | 2007002261 A2 | 1/2007 |
| WO | 2008098796 A1 | 8/2008 |
| WO | 2012/121679 A1 | 9/2012 |
| WO | 2012135345 A1 | 10/2012 |
| WO | 2013122544 A2 | 8/2013 |
| WO | 2016008851 A1 | 1/2016 |
| WO | 2016/183176 A1 | 11/2016 |
| WO | 2017/019896 A1 | 2/2017 |
| WO | 2018/234879 A1 | 12/2018 |
| WO | 2018/235056 A1 | 12/2018 |
| WO | 2020039401 A1 | 2/2020 |

OTHER PUBLICATIONS

Binz et al., Designing repeat proteins: well-expressed, soluble and stable proteins from combinatorial libraries of consensus ankyrin repeat proteins. J Mol Biol. Sep. 12, 2003;332(2):489-503.
Borghouts et al., Peptide aptamers: recent developments for cancer therapy. Expert Opin Biol Ther. Jun. 2005;5(6):783-97.
Braddock, 11th annual Inflammatory and Immune Diseases Drug Discovery and Development Summit Mar. 12-13, 2007, San Francisco, USA. Expert Opin Investig Drugs. Jun. 2007; 16(6):909-17.
Chothia et al., Conformations of immunoglobulin hypervariable regions. Nature. Dec. 21-28, 1989;342(6252):877-83.
Extended European Search Report, European Application No. 20163420.1, dated Sep. 24, 2020, 8 pages.
Final Decision of Rejection for Japanese Application No. 2014-557603, dated Dec. 19, 2017.
Geiger et al., Neutralization of interleukin-1 beta activity in vivo with a monoclonal antibody alleviates collagen-induced arthritis in DBA/1 mice and prevents the associated acute-phase response. Clin Exp Rheumatol. Sep.-Oct. 1993;11(5):515-22.
Goh, A. et al., "A novel human anti-interleukin-1[beta] neutralizing monoclonal antibody showing in vivo efficacy," MABS, vol. 6(3):764-772 (2014).
Holliger et al., Engineered antibody fragments and the rise of single domains. Nat Biotechnol. Sep. 2005;23(9):1126-36.
Hosse et al., A new generation of protein display scaffolds for molecular recognition. Protein Sci. Jan. 2006;15(1):14-27.
International Preliminary Report on Patentability dated Feb. 26, 2015 for PCT/SG2013/000057.
International Search Report and Written Opinion dated May 16, 2013 for PCT/SG2013/000057.
Irving et al., Ribosome display and affinity maturation: from antibodies to single V-domains and steps towards cancer therapeutics. J Immunol Methods. Feb. 1, 2001;248(1-2):31-45.
Kohl et al., Designed to be stable: crystal structure of a consensus ankyrin repeat protein. Proc Natl Acad Sci U S A. Feb. 18, 2003;100(4):1700-5. Epub Feb. 3, 2003.
Lederman et al., A single amino acid substitution in a common African allele of the CD4 molecule ablates binding of the monoclonal antibody, OKT4. Mol Immunol. Nov. 1991;28(11):1171-81. PubMed PMID: 1961196.
Li et al., Temporal associations between interleukin 22 and the extracellular domains of IL-22R and IL-10R2. Int Immunopharmacol. May 2004;4(5):693-708. Review. PubMed PMID: 15120653.
Myers et al., Optimal alignments in linear space. Comput Appl Biosci. Mar. 1988;4(1):11-7.
Needleman et al., A general method applicable to the search for similarities in the amino acid sequence of two proteins. J Mol Biol. Mar. 1970;48(3):443-53.
Osborn et al., Treatment with an Interleukin 1 beta antibody improves glycemic control in diet-induced obesity. Cytokine. Oct. 2008;44(1):141-8. Epub Aug. 23, 2008.
Owyang et al., XOMA 052, a potent, high-affinity monoclonal antibody for the treatment of IL-1.beta.-mediated diseases. Mabs, vol. 3(1):49-60 (2011).
Panka et al., Variable region framework differences result in decreased or increased affinity of variant anti-digoxin antibodies. Proc Natl Acad Sci U S A. May 1988;85(9):3080-4. PubMed PMID: 3129726; PubMed Central PMCID: PMC280147.
Parker et al., Antibody mimics based on human fibronectin type three domain engineered for thermostability and high-affinity binding to vascular endothelial growth factor receptor two. Protein Eng Des Sel. Sep. 2005;18(9):435-44. Epub Aug. 8, 2005.
Rudikoff et al., Single amino acid substitution altering antigen-binding specificity. Proc Natl Acad Sci U S A. Mar. 1982;79(6):1979-83. PubMed PMID: 6804947; PubMed Central PMCID: PMC346105.
Silverman et al., Multivalent avimer proteins evolved by exon shuffling of a family of human receptor domains. Nat Biotechnol. Dec. 2005;23(12):1556-61. Epub Nov. 20, 2005.
Skerra, Lipocalins as a scaffold. Biochim Biophys Acta. Oct. 18, 2000;1482(1-2):337-50.
Supplementary European Search Report for Application No. EP 13748708.8, dated Mar. 4, 2016.
Wikman et al., Selection and characterization of HER2/neu-binding affibody ligands. Protein Eng Des Sel. May 2004;17(5):455-62. Epub Jun. 18, 2004.
Zahnd et al., A designed ankyrin repeat protein evolved to picomolar affinity to Her2. J Mol Biol. Jun. 15, 2007;369(4):1015-28. Epub Mar. 20, 2007.
U.S. Appl. No. 16/192,537, filed Nov. 15, 2018, Cheng-I Wang.
U.S. Appl. No. 14/378,442, filed Aug. 13, 2014, Cheng-I Wang.
U.S. Appl. No. 17/061,194, filed Oct. 1, 2020, Cheng-I Wang.
U.S. Appl. No. 17/150,691, filed Jan. 15, 2021, Cheng-I Wang.
U.S. Appl. No. 16/192,537, Oct. 7, 2020, P. Mertz.
U.S. Appl. No. 16/192,537, Apr. 10, 2020, P. Mertz.
U.S. Appl. No. 14/378,442, Aug. 13, 2018, P. Mertz.
U.S. Appl. No. 14/378,442, Feb. 20, 2018, P. Mertz.
U.S. Appl. No. 14/378,442, Feb. 9, 2018, P. Mertz.
U.S. Appl. No. 14/378,442, Jun. 28, 2017, P. Mertz.
U.S. Appl. No. 14/378,442, Jan. 5, 2017, P. Mertz.
U.S. Appl. No. 14/378,442, Aug. 18, 2016, P. Mertz.

Fig. 2

1H_light chain

AATTTTATGCTGACTCAGCCCCACTCTGTGTCGGAGTCTCCGGGGAAGACGGTGACCATCCC
CTGCACCGCCAGCAGTGGCAGCATTGCCAACAACTTTGTGCAGTGGTACCAGCAGCGCCCG
GGCAGTGCCCCCACCACTGTGATCTATGAGGATAGTCAAAGACCCTCTGGGGTCCCTGATCG
GTCTCTGGCTCCATCGACAGCTCCTCCAACTCTGCCTCCCTCACCATCTCTGGACTGAAGAC
TGAGGACGAGGCTGATTATTACTGTCAGTCTTATGATAGTGCCAATGACAGGGTGACATTCGG
CGGAGGGACCAAGCTGATCGTCCTCGGTCAGCCCAAGGCTGCCCCCTCGGTCACTCTGTTCC
CGCCCTCCTCTGAGGAGCTTCAAGCCAACAAGGCCACACTGGTGTGTCTCATAAGTGACTTCT
ACCCGGGAGCCGTGACAGTGGCCTGGAAGGCAGATAGCAGCCCCGTCAAGGCGGGAGTGG
AGACCACCACACCCTCCAAACAAAGCAACAACAAGTACGCGGCCAGCAGCTATCTGAGCCTG
ACGCCTGAGCAGTGGAAGTCCCACAGAAGCTACAGCTGCCAGGTCACGCATGAAGGGAGCA
CCGTGGAGAAGACAGTGGCCCCTGCAGAATGCTCT

NFMLTQPHSVSESPGKTVTIPCTASSGSIANNFVQWYQQRPGSAPTTVIYEDSQRPSGVPDRVSG
SIDSSSNSASLTISGLKTEDEADYYCQSYDSANDRVTFGGGTKLIVLGQPKAAPSVTLFPPSSEELQ
ANKATLVCLISDFYPGAVTVAWKADSSPVKAGVETTTPSKQSNNKYAASSYLSLTPEQWKSHRSY
SCQVTHEGSTVEKTVAPAECS

1H_heavy chain

GAGGTGCAGCTGGTACAGTCTGGGGCTGAGGTGAAGAAGCCTGGGGCCTCAGTGAAGGTTT
CCTGCAAGGCATCTGGATACACCTTCACCAGCTACTATATGCACTGGGTGCGACAGGCCCCT
GGACAAGGGCTTGAGTGGATGGGACTTGTTGATCCTGAAGATGGTGAAACAATATACGCAGA
GAAGTTCCAGGGCAGAGTCACCATAACCGCGGACACGTCTACAGACACAGCCTACATGGAGC
TGAGCAGCCTGAGATCTGAGGACACGGCCGTGTATTACTGTGCGAGATTGACTGGGTGGCT
GGTACGGAAGGTTGGGGTACTACTTTGACTACTGGGGCCAGGGAACCCTGGTCACCGTCTC
AAGCGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGTGTC
GTGGAACTCAGGCGCCCTGACCAGCGGCGTCCACACCTTCCCGGCTGTCCTACAGTCCTCAG
GACTCTACTCCCTCAGCAGCGTAGTGACCGTGCCCTCCAGCAGCTTGGGCACCCAGACCTAC
ATCTGCAACGTGAATCACAAGCCCAGCAACACCAAGGTGGACAAGAAAGTTGAGCCCAAATCT
TGT

EVQLVQSGAEVKKPGASVKVSCKASGYTFTSYYMHWVRQAPGQGLEWMGLVDPEDGETIYAEK
FQGRVTITADTSTDTAYMELSSLRSEDTAVYYCARLTGWLVRKVGYYFDYWGQGTLVTVSSAS
TKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSC

Fig. 2 (Continued)

2H_light chain

CAGTCTGTGTTGACGCAGCCGCCCTCAGTGTCCGTGTCCCCAGGACAGACAGCCAGCATCAC
CTGCTCTGGAGATAAATTGGGGGATAAATTTGCTTTCTGGTATCAGCAGAAGCCAGGCCAGTC
CCTGTTTTGGTCATCTATCTAGATAACAAGCGGCCCTCAGGGATCCCTGAGCGATTCTCTGG
CTCCAACTCTGGGAACACAGCCACTCTGACCATCAGCGGGACCCAGGCTTTGGATGAGGCTG
ACTACTACTGTCAGGCGTGGGACAGCAACATTGAAGTATTCGGCGGAGGGACCAAGCTGACC
GTCCTAGGTCAGCCCAAGGCTGCCCCTCGGTCACTCTGTTCCCGCCCTCCTCTGAGGAGCT
TCAAGCCAACAAGGCCACACTGGTGTGTCTCATAAGTGACTTCTACCCGGGAGCTGTGACAG
TGGCCTGGAAGGCAGATAGCAGCCCCGTCAAGGCGGGAGTGGAGACCACCACACCCTCCAA
ACAAAGCAACAACAAGTACGCGGCCAGCAGCTACCTGAGCCTGACGCCTGAGCAGTGGAAGT
CCCACAAAAGCTACAGCTGCCAGGTCACGCATGAAGGGAGCACCGTGGAGAAGACAGTGGC
CCCTACAGAATGTTCA

QSVLTQPPSVSVSPGQTASITCSGDKLGDKFAFWYQQKPGQSPVLVIYLDNKRPSGIPERFSGSN
SGNTATLTISGTQALDEADYYCQAWDSNIEVFGGGTKLTVLGQPKAAPSVTLFPPSSEELQANKAT
LVCLISDFYPGAVTVAWKADSSPVKAGVETTTPSKQSNNKYAASSYLSLTPEQWKSHKSYSCQVT
HEGSTVEKTVAPTECS

2H_heavy chain

CAGGTGCAGCTACAGCAGTGGGGCGCAGGACTGTTGAAGCCCTCGGAGACCCTGTCCCTCA
CCTGCGCTGTCTATGGTGGGTCCTTCAGTGATTACTACTGGAGCTGGATCCGCCAGCCCCCA
GGGAAGGGGCTAGAGTGGATTGGGGAAATCGATCATAGTGGAAGCACCAACTACAACCCGTC
CCTCAAGAGTCGAGTCACCATATCAGTAGACACGTCCAGGAACCAGTTCTCCCTGAGCCTGA
GCTCTGTGACCGCCGCGGACACGGCTGTTTATTACTGTGCGAGAGCGTCCCCGACCACTGG
TGGACCCTTGACTACTGGGGCCAGGGCACCCTGGTCACCGTCTCAAGCGCCTCCACCAAG
GGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGC
CCTGACCAGCGGCGTCCACACCTTCCCGGCTGTCCTACAGTCCTCAGGACTCTACTCCCTCA
GCAGCGTAGTGACCGTGCCCTCCAGCAGCTTGGGCACCCAGACCTACATCTGCAACGTGAAT
CACAAGCCCAGCAACACCAAGGTGGACAAGAAAGTTGAGCCCAAATCTTGT

QVQLQQWGAGLLKPSETLSLTCAVYGGSFSDYYWSWIRQPPGKGLEWIGEIDHSGSTNYNPSLK
SRVTISVDTSRNQFSLSLSSVTAADTAVYYCARASPSSGWTLDYWGQGTLVTVSSASTKGPSVFP
LAPSSKSTSGGTAALGCLVKDYFPEPVTVSWNSGALTSGVHTFPAVLQSSGLYSLSSVVTVPSSS
LGTQTYICNVNHKPSNTKVDKKVEPKSC

Fig. 10

- Heavy variable region:

QVQLQQWGAGLLKPSETLSLTCAVYGGSFS<u>DYYWS</u>WIRQPPGKGLEWIG<u>EIDHSGSTNYNP
SLKS</u>RVTISVDTS<u>K</u>NQFSL<u>K</u>LSSVTAADTAVYYCAR<u>ASPSSGWTLDY</u>WGQGTL

- Light variable (identical to P2D7):

QSVLTQPPSVSVSPGQTASITCS<u>GDKLGDKFAF</u>WYQQKPGQSPVLVIY<u>LDNKRPS</u>GIPERFSG
SNSGNTATLTISGTQALDEADYYC<u>YAWADTYEVF</u>GGGTK

With: ........ CDR1, _ _ _ _ _ CDR2, ════ CDR3.

IL-1β NEUTRALIZING HUMAN MONOCLONAL ANTIBODIES

CROSS REFERENCE TO RELATED APPLICATIONS

This application is a divisional of U.S. patent application Ser. No. 16/192,537, filed Nov. 15, 2018, which is a divisional of U.S. patent application Ser. No. 14/378,442, filed Aug. 13, 2014, now U.S. Pat. No. 10,167,335, which is a U.S. National Stage of International Patent Application No. PCT/SG2013/000057, filed Feb. 13, 2013, which claims the benefit of priority to Singapore Patent Application No. 201201007-0, filed Feb. 13, 2012. The entire contents of each of the aforementioned applications are incorporated by reference herein in their entireties.

REFERENCE TO SEQUENCE LISTING

The instant application contains a Sequence Listing which has been submitted electronically in ASCII format and is hereby incorporated by reference in its entirety. Said ASCII copy, created Dec. 23, 2020, is named "FBN-003USDVAD-V_Sequence-Listing.txt" and is 22,709 bytes in size.

TECHNICAL FIELD

The present invention relates to antigen binding proteins and in particular to IL-1β antigen binding proteins. More specifically, the present invention relates to sequences of the binding proteins and the heavy and light chains. Compositions comprising the antigen binding proteins, use of the antigen binding proteins and methods for production are also provided.

BACKGROUND

Interleukin-1 beta (IL-1β) is a member of the Interleukin-1 cytokine family and is an important mediator of the inflammatory response. It is a pro-inflammatory cytokine and is involved in the proliferation, differentiation and apoptosis of cells.

Overexpression of IL-1β has been implicated in a number of inflammatory and autoimmune diseases such as cryopyrin-associated periodic syndromes and related disorders, diabetes, Crohn's disease, rheumatoid arthritis, renal cell carcinoma, gout and inflammatory acne.

It is an aim of the present invention to provide antigen binding proteins specific to IL-1β that are able to neutralize the activity of IL-1β to prevent or treat diseases associated with heightened IL-1β production.

To date, three biologicals targeting the IL-1β signalling pathway have been approved for clinical use: anakinra (an IL-1 receptor antagonist), rilonacept (a fusion protein comprising the IL-1 receptor 1) and canakinumab (a monoclonal antibody).

In addition to the three approved IL-1 blockers mentioned above, the humanized monoclonal antibody XOMA-052 (gevokizumab) is currently in clinical development. Each molecule exhibits unique mechanisms of action and displays different cross-reactivity and pharmacological profile.

SUMMARY

According to a first aspect, there is provided an isolated IL-1β specific antigen binding protein comprising one or more binding units selected from the group consisting of the following binding units:

(i) a binding unit L1 comprising Kabat residues 23-35 of SEQ ID NO: 3 or Kabat residues 24-33 of SEQ ID NO: 4, 15 or 16, or a variant thereof which contains at least one amino acid substitution, insertion or deletion in the binding unit L1;
(ii) a binding unit L2 comprising Kabat residues 51-57 of SEQ ID NO: 3 or Kabat residues 49-55 of SEQ ID NO: 4, 15 or 16, or a variant thereof which contains at least one amino acid substitution, insertion or deletion in the binding unit L2;
(iii) a binding unit L3 comprising Kabat residues 92-102 of SEQ ID NO: 3 or Kabat residues 88-96 of SEQ ID NO: 4, 15 or 16, or a variant thereof which contains at least one amino acid substitution, insertion or deletion in the binding unit L3;
(iv) a binding unit H1 comprising Kabat residues 31-35 of SEQ ID NO: 1 or Kabat residues 31-35 of SEQ ID NO: 2 or 14, or a variant thereof which contains at least one amino acid substitution, insertion or deletion in the binding unit H1;
(v) a binding unit H2 comprising Kabat residues 50-66 of SEQ ID NO: 1 or Kabat residues 50-65 of SEQ ID NO: 2 or 14, or a variant thereof which contains at least one amino acid substitution, insertion or deletion in the binding unit H2; and
(vi) a binding unit H3 comprising Kabat residues 99-114 of SEQ ID NO: 1 or Kabat residues 98-108 of SEQ ID NO: 2 or 14, or a variant thereof which contains at least one amino acid substitution, insertion or deletion in the binding unit H3.

According to the second aspect, there is provided an isolated, IL-1β specific antigen binding protein that neutralizes IL-1β in a cell stimulation assay at an IC50 value of less than 20 nM, less than 15 nM, less than 10 nM, less than 5 nM, less than 3 nM, less than 1 nM, less than 0.5 nM or less than 0.2 nM.

According to a third aspect, there is provided an isolated IL-1β specific antigen binding protein that inhibits IL-1β induced IL-6 production in a cell inhibition assay at an IC50 value of less than 20 nM, less than 15 nM, less than 10 nM, less than 5 nM, less than 4 nM, less than 3 nM, less than 1 nM, less than 0.5 nM or less than 0.4 nM.

According to a fourth aspect, there is provided an isolated, IL-1β specific antigen binding protein that binds IL-1β with a $K_D$ value of less than 10 nM, less than 5 nM, less than 2 nM, less than 1 nM, less than 0.5 nM, or less than 0.1 nM.

According to a fifth aspect, there is provided an isolated, IL-1β specific antigen binding protein that neutralizes human IL-4 at an IC50 value of from 1 pM to 100 pM.

According to a sixth aspect, there is provided an isolated, IL-1β specific antigen binding protein that neutralizes murine IL-1β at an IC50 value of from 100 pM to 1000 pM.

According to a seventh aspect, there is provided an isolated, IL-1β specific antigen binding protein wherein said binding protein has an affinity (KD) to human IL-1β of from 1 pM to 100 pM.

According to an eighth aspect, there is provided an isolated, IL-1β specific antigen binding protein wherein said binding protein has an affinity (KD) to murine IL-1β of from 5 pM to 200 pM.

According to a ninth aspect, there is provided an isolated antigen binding protein of any one of the preceding claims, for use in treating cancer, an inflammatory disease or an autoimmune disease selected from the group consisting of arthritis, inflammatory bowel disease, Crohn's disease, rheumatoid arthritis, gout, diabetes, uveitis, cryopyrin-associated periodic syndromes and inflammatory acne.

According to a tenth aspect, there is provided a use of the isolated antigen binding protein as defined above, in the preparation of a medicament for the treatment of cancer, an inflammatory disease or an autoimmune disease selected from the group consisting of arthritis, inflammatory bowel disease, Crohn's disease, rheumatoid arthritis, gout, diabetes, uveitis, cryopyrin-associated periodic syndromes and inflammatory acne.

According to an eleventh aspect, there is provided a composition comprising the antigen binding protein as defined above and a pharmaceutically acceptable carrier.

According to a twelfth aspect, there is provided an isolated cell line that is capable of producing the antigen binding protein as defined above.

According to a thirteenth aspect, there is provided an isolated nucleic acid molecule comprising or consisting of sequences selected from SEQ ID NO:1 or SEQ ID NO:2 or 14, or fragments thereof.

According to a fourteenth aspect, there is provided an isolated nucleic acid molecule comprising or consisting of sequences selected from SEQ ID NO:3 or SEQ ID NO:4, 15 or 16, or fragments thereof.

According to a fifteenth aspect, there is provided a vector comprising the nucleic acid molecule as defined above.

According to a sixteenth aspect, there is provided a host cell comprising the nucleic acid molecule as defined above.

According to a seventeenth aspect, there is provided a host cell comprising the vector as defined above.

According to an eighteenth aspect, there is provided a method of producing an antigen binding protein as defined above, comprising culturing the host cell as defined above under suitable conditions and recovering said protein therefrom.

According to a nineteenth aspect, there is provided a method of treating cancer, an inflammatory disease or an autoimmune disease selected from the group consisting of arthritis, inflammatory bowel disease, Crohn's disease, rheumatoid arthritis, gout, diabetes, uveitis, cryopyrin-associated periodic syndromes and inflammatory acne, wherein the isolated antigen binding protein as defined above is administered to a subject.

DEFINITIONS

The following words and terms used herein shall have the meaning indicated:

The term "antigen binding protein" as used herein refers to antibodies, antibody fragments and other protein constructs, such as domains, which are capable of binding to IL-1β☐

The term "antibody" as used herein in the broadest sense to refer to molecules with an immunoglobulin-like domain and includes monoclonal, recombinant, polyclonal, chimeric, humanised, bispecific, multispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. The domain may be a domain antibody or may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than its natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include up to 25 amino acids without affecting the overall fold of the microprotein. For further details of engineered knottin domains, see WO2008098796.

Other binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Binding domains of the present invention could be derived from any of these alternative protein domains.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The term "neutralises" as used throughout the present specification means that the biological activity of IL-1β is reduced in the presence of an antigen binding protein as described herein in comparison to the activity of IL-1β in the absence of the antigen binding protein, in vitro or in vivo. Neutralisation may be due to one or more of blocking IL-1β binding to its receptor, preventing IL-1β from activating its receptor, down regulating IL-1β or its receptor, or affecting effector functionality.

The reduction or inhibition in biological activity may be partial or total. A neutralising antigen binding protein may neutralise the activity of IL-1β by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to IL-1β activity in the absence of the antigen binding protein.

Neutralisation may be determined or measured using one or more assays known to the skilled person or as described herein. For example, antigen binding protein binding to IL-1β can be assessed in a sandwich ELISA, by BIAcore™, FMAT, FORTEbio, or similar in vitro assays, but also in cell-based functional assays.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

The table below represents one definition using each numbering convention for each CDR or binding unit. The Kabat numbering scheme is used in Table 1 to number the variable domain amino acid sequence. It should be noted that some of the CDR definitions may vary depending on the individual publication used.

|    | Kabat CDR       | Chothia CDR | AbM CDR    | Contact CDR | Minimum binding unit |
|----|-----------------|-------------|------------|-------------|----------------------|
| H1 | 31-35/35A/35B   | 26-32/33/34 | 26-35/35A/35B | 30-35/35A/35B | 31-32             |
| H2 | 50-65           | 52-56       | 50-58      | 47-58       | 52-56                |
| H3 | 95-102          | 95-102      | 95-102     | 93-101      | 95-101               |
| L1 | 24-34           | 24-34       | 24-34      | 30-36       | 30-34                |
| L2 | 50-56           | 50-56       | 50-56      | 46-55       | 50-55                |
| L3 | 89-97           | 89-97       | 89-97      | 89-96       | 89-96                |

For nucleotide and amino acid sequences, the term "identical" or "sequence identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence as described herein (see for example SEQ ID NO: X), that is be 100% identical, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in a reference polynucleotide sequence, by the numerical percent of the respective percent identity (divided by 100) and subtracting that product from said total number of nucleotides in the reference polynucleotide sequence as follows:

$$n_n \leq x_n - (x_n \cdot y),$$

wherein $n_n$ is the number of nucleotide alterations, $x_n$ is the total number of nucleotides in the reference polynucleotide sequence and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, · is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence, that is be 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence by the numerical percent of the respective percent identity (divided by 100) and then subtracting that product from said total number of amino acids in the polypeptide reference sequence as follows:

$$n_a \leq x_a - (x_a \cdot y),$$

wherein $n_a$ is the number of amino acid alterations, $x_a$ is the total number of amino acids in the reference polypeptide sequence and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, · is the symbol for the multiplication operator, and wherein any non-integer product of $x_a$ and y is rounded down to the nearest integer prior to subtracting it from $x_a$. The % identity may be determined across the length of the sequence.

The term "specifically binds" as used throughout the present specification in relation to antigen binding proteins means that the antigen binding protein binds to a target epitope on IL-1β with a greater affinity than that which results when bound to a non-target epitope. In certain embodiments, specific binding refers to binding to a target with an affinity that is at least 10, 50, 100, 250, 500, or 1000 times greater than the affinity for a non-target epitope. For example, binding affinity may be as measured by routine methods, e.g., by competition ELISA or by measurement of Kd with BIACORE™, KINEXA™ or PROTEON™.

The term "IC50" as used herein means the molar concentration of a substance (antagonist) that reduces the efficacy of a reference agonist or the constitutive activity of a biological target by 50% of an antagonist curve (Top-Bottom) for a particular test substance.

The term "EC50" as used herein means the molar concentration of a substance (agonist) that induces a response by 50% of the maximal effect of a dose-response curve.

Throughout this specification, amino acid residues in variable domain sequences and full length antibody sequences are numbered according to the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

The term "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage.

Nucleic acid as used herein means any single or double-stranded RNA or DNA molecule, such as mRNA, cDNA, and genomic DNA.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure of Optional Embodiments

Exemplary, non-limiting embodiments of an isolated IL-1β specific antigen binding protein will now be disclosed.

In one embodiment the isolated IL-1β specific antigen binding protein comprises one or more binding units selected from the group consisting of the following binding units:
  (i) a binding unit L1 comprising Kabat residues 23-35 of SEQ ID NO: 3 or Kabat residues 24-33 of SEQ ID NO: 4, 15 or 16, or a variant thereof which contains at least one amino acid substitution, insertion or deletion in the binding unit L1;
  (ii) a binding unit L2 comprising Kabat residues 51-57 of SEQ ID NO: 3 or Kabat residues 49-55 of SEQ ID NO: 4, 15 or 16, or a variant thereof which contains at least one amino acid substitution, insertion or deletion in the binding unit L2;
  (iii) a binding unit L3 comprising Kabat residues 92-102 of SEQ ID NO: 3 or Kabat residues 88-96 of SEQ ID NO: 4, 15 or 16, or a variant thereof which contains at least one amino acid substitution, insertion or deletion in the binding unit L3;
  (iv) a binding unit H1 comprising Kabat residues 31-35 of SEQ ID NO: 1 or Kabat residues 31-35 of SEQ ID NO: 2 or 14, or a variant thereof which contains at least one amino acid substitution, insertion or deletion in the binding unit H1;
  (v) a binding unit H2 comprising Kabat residues 50-66 of SEQ ID NO: 1 or Kabat residues 50-65 of SEQ ID NO: 2 or 14, or a variant thereof which contains at least one amino acid substitution, insertion or deletion in the binding unit H2; and
  (vi) a binding unit H3 comprising Kabat residues 99-114 of SEQ ID NO: 1 or Kabat residues 98-108 of SEQ ID NO: 2 or 14, or a variant thereof which contains at least one amino acid substitution, insertion or deletion in the binding unit H3.

In one embodiment the isolated IL-1β specific antigen binding protein comprises a heavy chain and/or a light chain in which the heavy chain comprises or consists of an amino acid sequence encoded by the nucleotide sequence selected from SEQ ID NO:1 or SEQ ID NO: 2 or 14 and in which the light chain comprises or consists of an amino acid sequence encoded by the nucleotide sequence selected from SEQ ID NO:3 or SEQ ID NO: 4, 15 or 16.

The heavy chain may be selected from the group consisting of α, δ, ε, γ and μ heavy chains. Preferably the heavy chain is γ.

The light chain is preferably selected from A or K light chains. Preferably the light chain is A.

In one embodiment, the Kabat residues 88-96 of SEQ ID NO: 4, 15 or 16 may be selected from residues consisting of the group selected from amino acids 1-9 of SEQ ID NO: 9, SEQ ID NO: 10, SEQ ID NO: 11, SEQ ID NO: 12 or SEQ ID NO: 13.

In one embodiment, the isolated IL-1β specific antigen binding protein neutralizes IL-1β in a cell function neutralization assay at an IC50 value of less than about 20 nM.

In another embodiment the isolated IL-1β specific antigen binding protein neutralizes IL-1β in a cell stimulation assay at an IC50 value of less than about 15 nM, less than about 10 nM, less than about 5 nM, less than about 3 nM, less than about 1 nM, less than about 0.5 nM, less than about 0.2 nM, less than about 100 pM, less than 50 pM, less than 10 pM, less than 5 pM or about 1 pM.

In some embodiments, the isolated IL-1β specific antigen binding protein is selected from human IL-1β and cross-reacts with murine or simian IL-1β.

In one embodiment, the isolated IL-1β specific antigen binding protein as described herein inhibits IL-1β induced IL-6 production in a cell inhibition assay at an IC50 value selected from less than about 20 nM. In another embodiment, the isolated IL-1β specific antigen binding protein described herein inhibits IL-1β induced IL-6 production in a cell inhibition assay at an IC50 value selected from less than about 15 nM, less than about 10 nM, less than about 5 nM, less than about 4 nM, less than about 3 nM, less than about 1 nM, less than about 0.5 nM or less than about 0.4 nM, less than about 300 pM, less than about 200 pM, less than about 100 pM, less than about 50 pM, less than about 10 pM or less than about 5 pM.

In one embodiment the isolated IL-1β specific antigen binding protein binds IL-1β with a $K_D$ value of less than about 10 nM. In another embodiment, the isolated IL-1β specific antigen binding protein binds IL-1β with a $K_D$ value of less than less than about 5 nM, less than about 2 nM, less than about 1 nM, less than about 0.5 nM, less than about 200 pM, less than about 100 pM, less than about 5 pM or less than about 1 pM.

In one embodiment, the isolated, IL-1β specific antigen binding protein neutralizes human IL-1β at an IC50 value of from 1 pM to 5 nM.

In one embodiment, the isolated, IL-1β specific antigen binding protein neutralizes murine IL-1β at an IC50 value of from 100 pM to 15 nM.

In one embodiment, the isolated antigen binding protein is capable of specifically binding to IL-1β.

In some embodiments, the isolated antigen binding protein comprises or consists of:
  (i) a heavy chain encoded by the nucleotide sequence of SEQ ID NO:1 and a light chain encoded by the nucleotide sequence of SEQ ID NO:3; or
  (ii) a heavy chain encoded by the nucleotide sequence of SEQ ID NO:2 or 14 and a light chain encoded by the nucleotide sequence of SEQ ID NO:4, 15 or 16.

In one embodiment the Kabat residues 88-96 of SEQ ID NO: 4, 15 or 16 may be selected from residues consisting of the group selected from amino acids 1-9 of SEQ ID 9, SEQ ID 10, SEQ ID 11, SEQ ID 12 or SEQ ID NO: 13.

In one embodiment, the isolated antigen binding protein or fragment thereof comprises or consists of a amino acid sequence having an identity selected from the group consisting of from at least 50%, at least 60%, at least 70%, at least 80% and at least 90% to SEQ ID NO: 1, 2, 14, 3, 4, 15 or 16.

In one embodiment, the isolated antigen binding protein is an antibody. Preferably, the antibody is monoclonal, polyclonal, bispecific or heteroconjugate.

In one embodiment, the antibody may be fully human.

In one embodiment the isolated antigen binding protein is an antibody selected from the subtype IgG1, IgG2, IgG4 or IgG3.

In one embodiment the isolated antigen binding protein is a single variable domain, a domain antibody, an antigen binding fragment, an immunologically effective fragment, a single chain Fv, a diabody or a tetravalent bispecific antibody (Tandab). In one embodiment, the antigen binding fragment may comprise an arrangement of one or more CDRs on non-antibody protein scaffolds such as a domain.

In one embodiment, the isolated antigen binding protein is recombinant.

In one embodiment, the isolated antigen binding protein comprises an agent selected from the group consisting of an immunoadhesion molecule, an imaging agent, a therapeutic agent and a cytotoxic agent.

The immunoadhesion molecules may comprise one or more of the immunoglobulin (Ig) superfamily of cell adhesion molecules (CAMs), integrins, cadherins, and selectins.

In one embodiment, the imaging agent may be selected from the group consisting of a radiolabel, an enzyme, a fluorescent label, a luminescent label, a bioluminescent label, a magnetic label and biotin.

Suitable examples of radiolabels include but are not limited to 32-Phosphorus or tritium in the form of tritiated thymidine.

Examples of suitable fluorescent labels include cyanine, fluorescein, rhodamine, Alexa Fluors, Dylight fluors, ATTO Dyes and BODIPY Dyes.

Examples of suitable luminescent labels include chemiluminescent labels including but not limited to luminol and Ruthenium probes and bioluminescent labels including but not limited to luciferin.

In one embodiment, the agent is a therapeutic or cytotoxic agent. The therapeutic or cytotoxic agent may be selected from the group consisting of an anti-metabolite, an alkylating agent, an antibiotic, a growth factor, a cytokine, an anti-angiogenic agent, an anti-mitotic agent, an anthracycline, toxin and an apoptotic agent.

In one embodiment, the isolated antigen binding protein is used in treating cancer, an inflammatory disease or an autoimmune disease selected from the group consisting or arthritis, inflammatory bowel disease, Crohn's disease, rheumatoid arthritis, gout, diabetes, uveitis, cryopyrin-associated periodic syndromes and inflammatory acne.

In one embodiment, the isolated antigen binding protein is used in the preparation of a medicament for the treatment of cancer, an inflammatory disease or an autoimmune disease selected from the group consisting of arthritis, inflammatory bowel disease, Crohn's disease, rheumatoid arthritis, gout, diabetes, uveitis, cryopyrin-associated periodic syndromes and inflammatory acne.

In one embodiment the cryopyrin-associated periodic syndromes may be selected from familial cold autoinflammatory syndrome (FCAS), Muckle-Wells syndrome (MWS), and neonatal-onset multisystem inflammatory disease (NOMID, also called chronic infantile neurologic cutaneous and articular syndrome or CINCA).

In one embodiment, there is provided a composition comprising the antigen binding protein as described herein and a pharmaceutically acceptable carrier.

In one embodiment, the antigen binding protein may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol and sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions, according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In one embodiment, the composition further comprises one or more therapeutic agents as described herein.

There is also provided an isolated cell line that is capable of producing the antigen binding protein as described herein.

Examples of cell lines capable of producing the antigen binding protein include HEK293 and CHO.

There is also provided an isolated nucleic acid molecule comprising or consisting of sequences selected from SEQ ID NO:1 or SEQ ID NO:2 or 14, or fragments thereof.

There is also provided an isolated nucleic acid molecule comprising or consisting of sequences selected from SEQ ID NO:3 or SEQ ID NO:4, 15 or 16, or fragments thereof.

In one embodiment, the isolated nucleic acid molecule or fragment thereof comprises or consists of a nucleotide sequence having an identity selected from the group consisting of from at least 50%, at least 60%, at least 70%, at least 80% and at least 90% to SEQ ID NO: 1, 2, 14, 3, 4, 15 or 16.

There is also provided a vector comprising the nucleic acid molecule as defined herein.

In one embodiment, the vector may be a plasmid or a virus. It will be appreciated by the person of skill in the art that many suitable vectors exist and are included in the scope of the present disclosure.

Preferably, the vector comprises an expression control sequence operably linked to said nucleic acid molecule.

The expression control sequence may be a nucleic acid fragment that promotes, enhances or represses expression of a gene or protein of interest.

There is also provided a host cell comprising the nucleic acid molecule as defined above.

The host cell may be a cultured cell line, an in vivo cell or an ex vivo cell.

In one embodiment, the host cell comprises the vector as described herein.

There is also provided a method of producing an antigen binding protein as described herein comprising culturing the host cell according as described herein under suitable conditions and recovering said protein therefrom.

There is also provided a method of treating cancer, an inflammatory disease or an autoimmune disease selected from the group consisting of arthritis, inflammatory bowel disease, Crohn's disease, rheumatoid arthritis, gout, diabetes, uveitis, cryopyrin-associated periodic syndromes and inflammatory acne, wherein the isolated antigen binding protein as described herein is administered to a subject.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 2 shows the sequencing results of the heavy and light chains of the 1H and 2H Fab clones. The sequences correspond to SEQ ID NOs: 7, 3, 5, 1, 8, 4, 6, and 14 from top to bottom.

FIG. 10 shows the sequence of P2D7KK. P2D7KK was derived from P2D7 by changing one arginine and one serine residue by lysine residues (bold and underlined) at positions 75 and 81 of the heavy chain variable region. The sequences correspond to SEQ ID NOs: 18 and 17 from top to bottom.

EXAMPLES

Non-limiting examples of the invention, including the best mode, and a comparative example will be further described in greater detail by reference to specific Examples, which should not be construed as in any way limiting the scope of the invention.

Example 1—Isolation of the Anti-Human IL-1β Antibodies and Characterization of the IL-1β Neutralization Capacity in Cell-Based Assays Anti-IL-1β antibodies were isolated from a human antibody phage display library (Humanyx HX-02 library) via in vitro selection. IL-1β specific monoclonal antibodies in the Fab format were initially identified by ELISA. These ELISA-positive Fabs were added to HEK-Blue™ IL-1β cells (InvivoGen, USA) which is an engineered HEK293 cell line that overexpresses recombinant human IL-1 receptor.

Binding of IL-1β to its receptor IL-1β on the surface of HEK-Blue™ IL-1β cells triggers a signaling cascade leading to the activation of NF-kB and the subsequent production of secreted alkaline phosphatase (SEAP). Detection of SEAP in the supernatant of HEK-Blue™ IL-1β cells can be readily assessed using QUANTI-Bluem™, a colorimetric SEAP substrate. The HEK-Blue cells are sensitive to both human and mouse IL-1β, but are insensitive to human IL-1α or INF-α.

Figure 1:
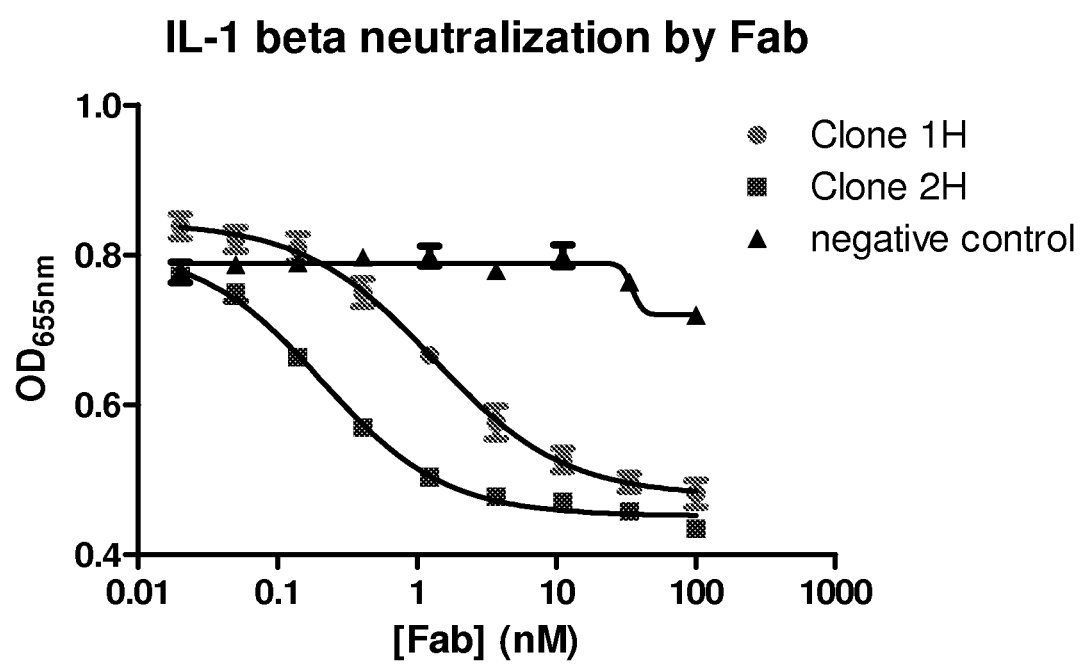
FIG. 1 shows the neutralization of IL-1β by Fab clones 1H and 2H. IL-1β neutralization was measured based on the optical density (OD) read at 655 nm and the concentration of Fab. The results show that clones 1H and 2H block the activation of IL-1β with an IC50 of 1.31 and 0.21 respectively.

Of the 22 ELISA-positive Fabs, two clones, 1H and 2H, were found to block the activation of the HEK-Blue IL-1β cells by IL-4 stimulation with $IC_{50}$ (concentration inhibiting 50% of IL-1β activity) of 1.31 and 0.21 nM, respectively (FIG. 1). Sequencing results revealed that both clones possessed λ light chain. Sequences of the heavy and light chains of clones 1H and 2H are shown in FIG. 2.

Example 2—Neutralization of IL-1β by IgG1 1H and 2H in the HEK-Blue Cell Assay

The two Fab clones 1H and 2H were converted into full length IgG by amplifying the heavy and light chains of each clone separately by PCR and cloning into the mammalian cell expression vector. The resulting plasmids, with human IgG1 subtype, were subsequently used for full length antibody expression by transient transfection into mammalian cells. Antibodies were purified by Protein G column.

Human IL-1β

Figure 3:
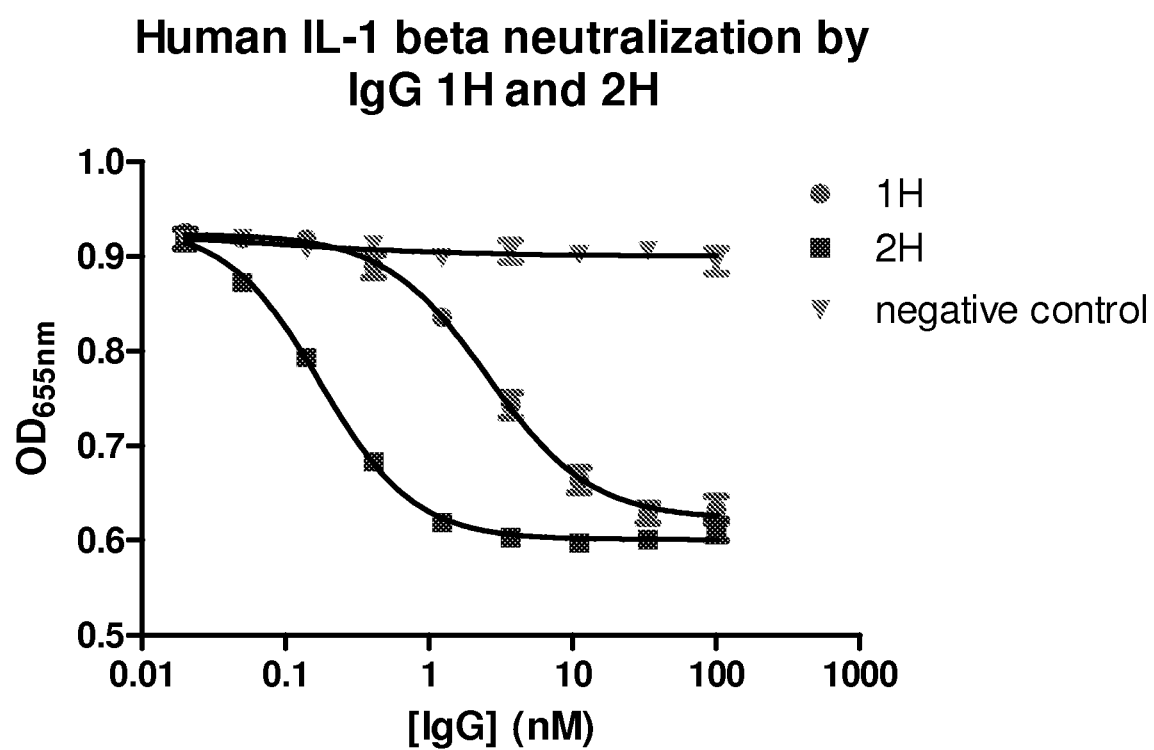
FIG. 3 shows the neutralization of human IL-1β by IgG1 1H and 2H. IL-1β neutralization was measured based on the optical density (OD) read at 655 nm and the concentration of IgG. The results show that clones 1H and 2H neutralize human IL-1β with a potency (EC50) of 2.6 nM and 0.17 nM respectively.

The neutralizing potency of the IgG clone 1H and 2H on human IL-1β was then assayed using HEK-Blue cells as described above. Cells were stimulated with 4 pM human IL-1β together with various concentrations of the antibody. The dose-response curve was fitted by the sigmoidal non-linear regression (variable slope) equation from which the $EC_{50}$ (the half maximal effective concentration) is calculated. In this assay clones 1H and 2H neutralized human IL-1β with potency ($EC_{50}$) of 2.6 nM and 0.17 nM, respectively (FIG. 3).

Mouse IL-1β

Figure 4:
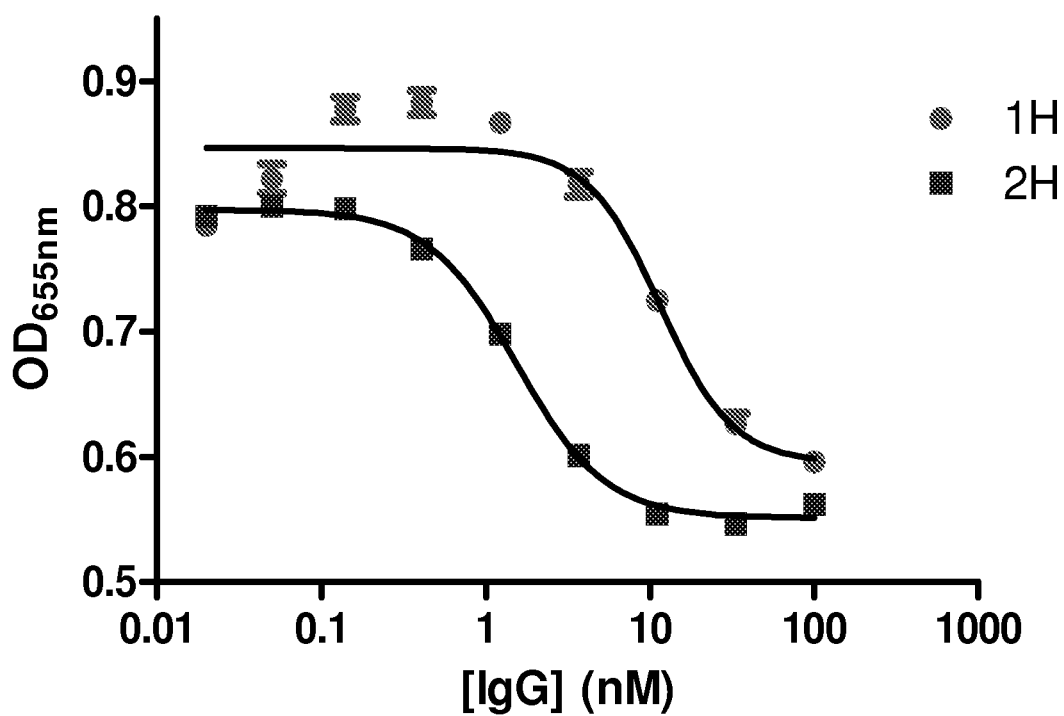
FIG. 4 shows the neutralization of mouse IL-1β by IgG1 1H and 2H. IL-1β neutralization was measured based on the optical density (OD) read at 655 nm and the concentration of IgG. The results show that clones 1H and 2H neutralized mouse IL-1β with a potency (EC50) of 11.5 nM and 1.5 nM respectively.

The neutralizing potency of the IgG clone 1H and 2H on mouse IL-1β was examined using HEK-Blue cells as described above. However, cells were stimulated with mouse IL-1β together with various concentrations of the antibody. In this assay clones 1H and 2H neutralized mouse IL-1β with potency ($EC_{50}$) of 11.5 nM and 1.5 nM, respectively (FIG. 4).

Example 3—Inhibition of Human IL-1β Induced IL-6 Production IgG 1H and 2H

In Vitro

Inhibition of human IL-1β induced IL-6 production by IgG 1H and 2H was examined in vitro using the human fibroblast cell line, MRC5. Stimulation of the human lung fibroblast cell, MRC5, by IL-1β results in IL-6 production.

Figure 5:
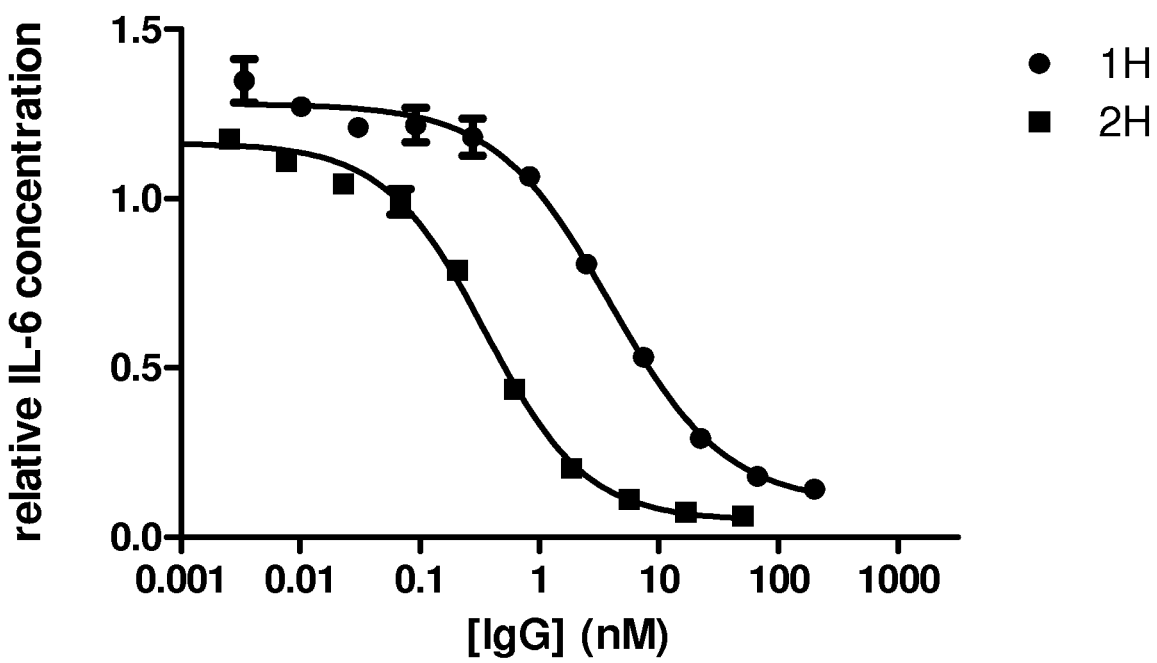
FIG. 5 shows that IgG 1H and 2H inhibit human IL-1β-induced IL-6 production in MRC5 cells. Human IL-1β neutralizing potency was determined by measuring the level of IL-6 produced in the presence of IgG 1H and 2H. MRC5 cells were stimulated by 4 pM of IL-1β together with various concentrations of IgG 1H and 2H. The results show that IgG 1H and 2H have an inhibition potency (EC50) of 3.92 nM and 0.35 nM respectively.

The human IL-1β neutralizing potency of IgG 1H and 2H was examined by measuring the level of IL-6 produced in the presence of the antibodies. Cells were stimulated with human IL-1β together with various concentrations of the antibodies, and the IL-6 was quantified by ELISA. In this assay, IgG 1H and 2H showed inhibition potency ($EC_{50}$) of 3.92 and 0.35 nM, respectively (FIG. 5).

In Vivo

Inhibition of human IL-1β induced IL-6 production by IgG 1H and 2H was examined in vivo in Balb/C mice. Administration of human IL-1β into Balb/c mice is followed by a rapid secretion of mouse IL-6 that is detectable in the serum by ELISA.

To assess the neutralizing potency of IgG 2H, mice were injected intraperitoneally with 4 or 20 mg/kg of 2H or with 400 μL of PBS. The following day, mice received human IL-1β or PBS (negative control). Two hours after IL-1β injection, blood was collected and IL-6 was measured in the serum by ELISA.

Figure 6:
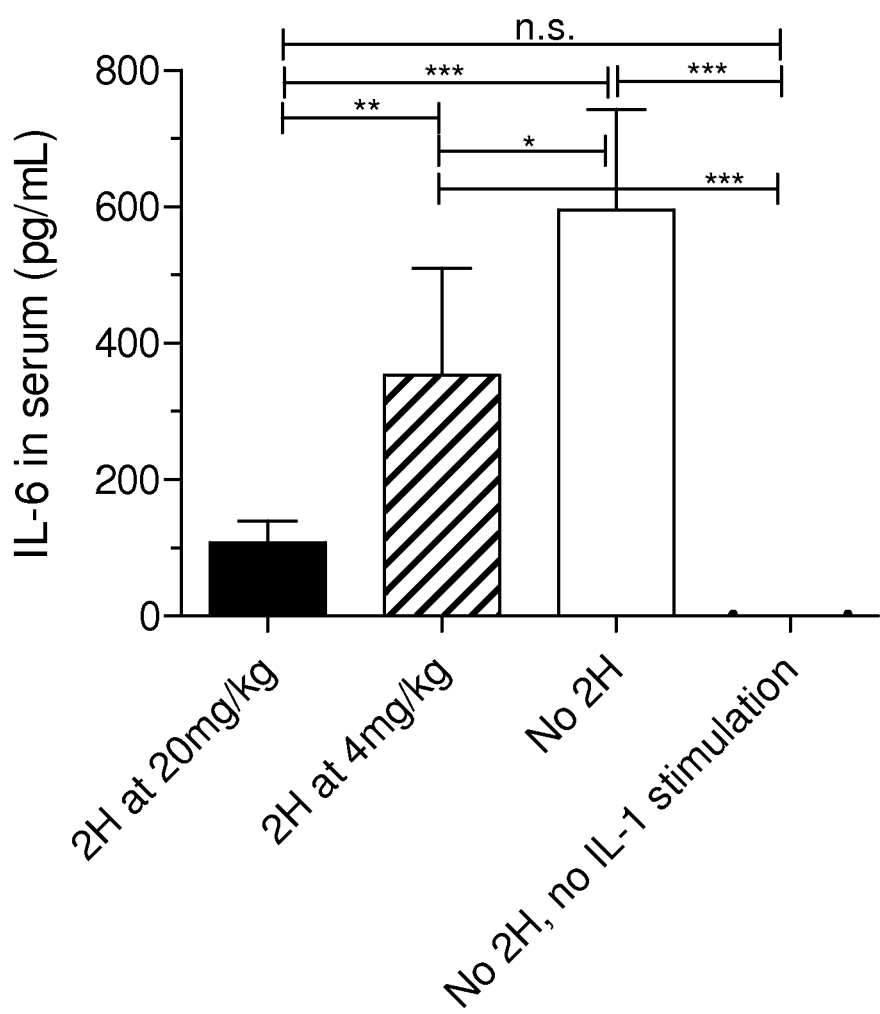
FIG. 6 shows that IgG 2H inhibits the human IL-1β induced IL-6 production in vivo in Balb/c mice. Neutralizing potency of IgG 2H was assessed by injecting mice intraperitoneally with 4 or 20 mg/kg of 2H or 400 μL of PBS and human IL-1β or PBS the following day. The blood was collected and IL-6 measured by ELISA. The results show that IgG 2H was able to inhibit human IL-1β induced production of IL-6 in mice in a dose dependent manner.

The results showed that 2H was able to inhibit the human IL-1β-induced production of IL-6 in mice in a dose-dependent manner (FIG. 6).

Example 4—Specificity of IgG 2H

Figure 7:
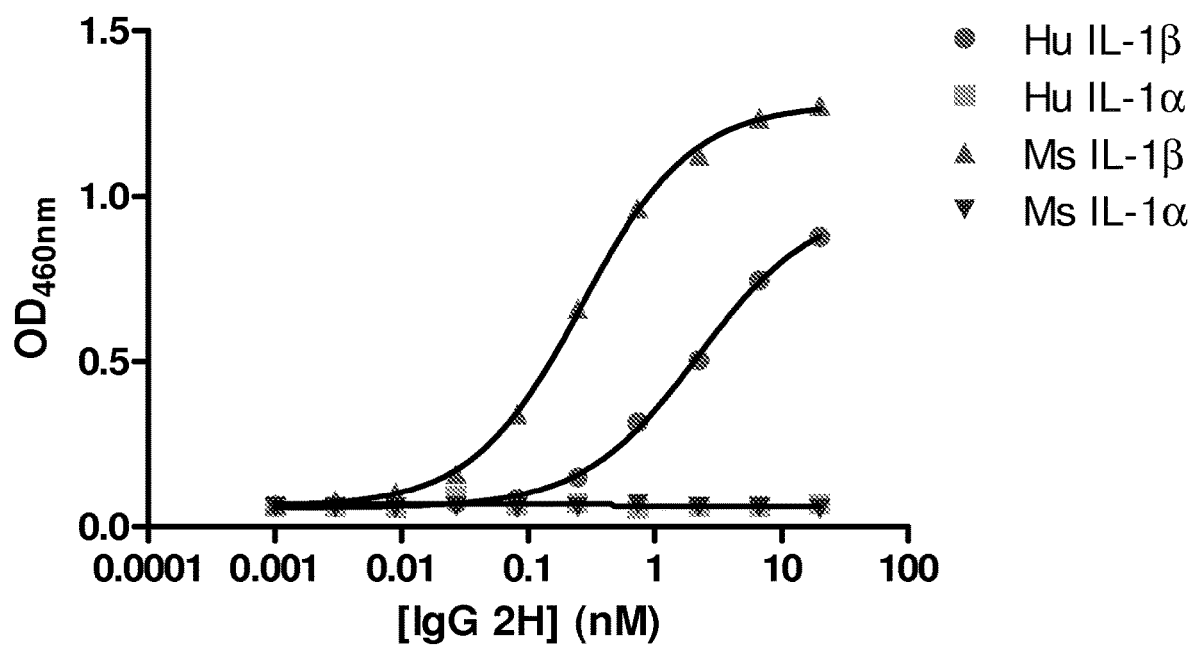
FIG. 7 shows that IgG 2H is specific for IL-1β and does not recognize IL-1α. Binding specificity of IgG 2H was determined based on the optical density (OD) at 460 nm and the concentration of IgG 2H. The results show that while IgG 2H bound to both human and mouse IL-1β in a dose dependent manner, it failed to bind to either human or mouse IL-1α.

The binding specificity of IgG 2H was examined against the two subtypes of IL-1, α and β, by direct ELISA. The results show that while IgG 2H bound to both human and mouse IL-1β in a dose dependent manner, it failed to bind to either human or mouse IL-1α at the concentration range tested (FIG. 7). Thus, IgG 2H displayed strong selectivity for IL-1β over IL-1α. Accordingly, IgG 2H is specific for IL-1β and does not recognize IL-1α.

Example 5—Affinity Maturation of IgG 2H

IgG 2H was affinity matured using the phage-display method and 5 matured clones with mutations in the CDR3 region of the light chain were selected after IL-1β neutralization assay on MRC5 cells.

Figure 8:
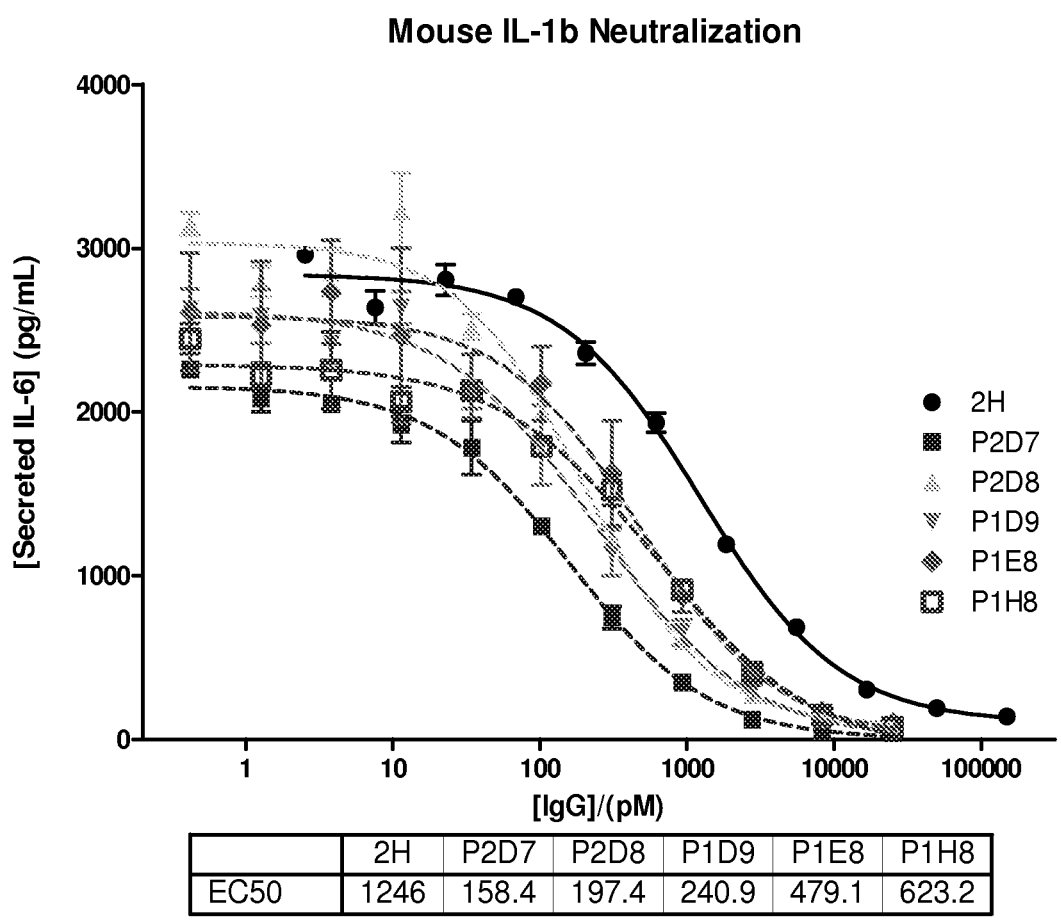
FIGS. 8 and 9 show the neutralization potency of 5 IgG clones obtained from the affinity maturation of IgG 2H. Neutralization potency was determined based on the concentration of secreted IL-against the concentration of each of the IgG clones. The results show that all matured IgG clones presented high neutralization potency for both mouse and human IL-1β. The results also show that matured clones were 2 to 8-fold more effective in neutralizing mouse IL-1β (FIG. 8) and 3 to 23-fold more effective in neutralizing human IL-1β (FIG. 9) than the non-matured IgG 2H.
Figure 9:
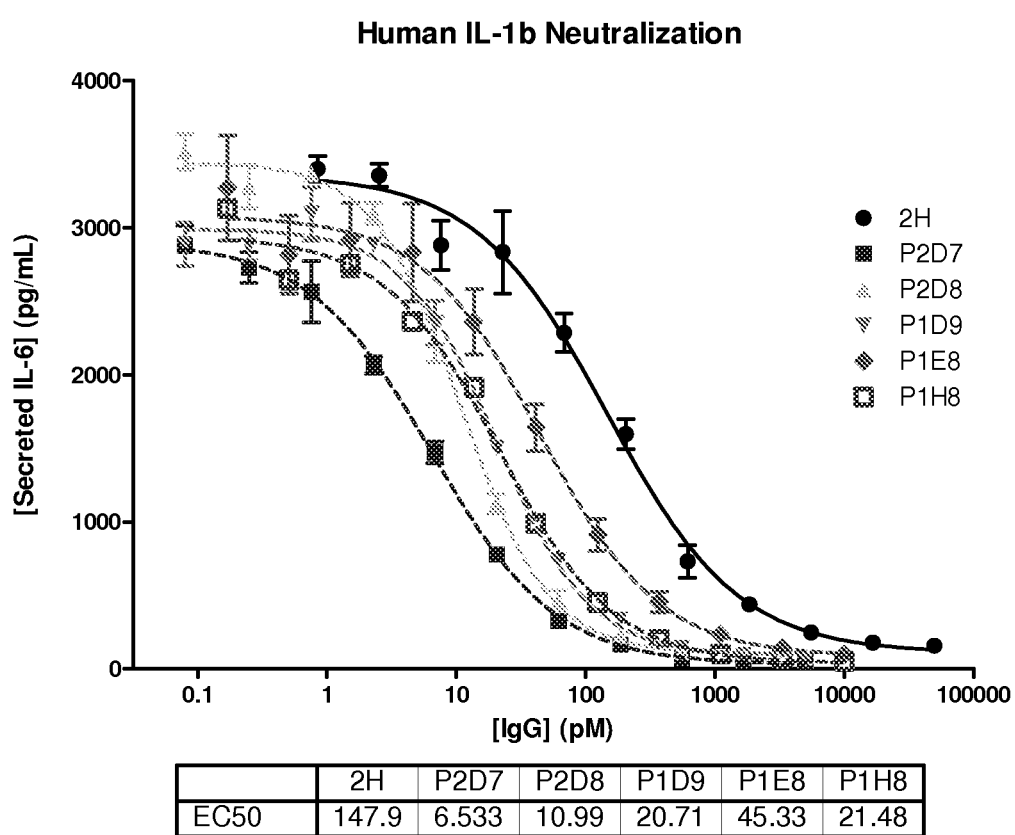

All matured IgG clones presented high neutralization potency for both mouse and human IL-1β in this assay. Matured clones were 2 to 8-fold more effective in neutralizing mouse IL-4 and 3 to 23-fold more effective in neutralizing human IL-1β than the initial IgG 2H, with potency ranging from $EC_{50}$ of 158.4 to 623.2 pM for the mouse cytokine (FIG. 8) and $EC_{50}$ from 6.5 to 45.3 pM for its human counterpart (FIG. 9)

Matured clones (except P1E8) were tested for affinity towards mouse and human IL-1β using the ProteOn bioanalyzer (BioRad, Hercules, USA).

The results showed that affinities for mouse IL-1β were 3 to 13-fold higher for matured clones compared to IgG 2H and 8 to 25-fold higher regarding human IL-1β, (Table 1).

TABLE 1

Affinities of matured clones towards mouse and human IL-1β compared to IgG 2H.

| | | Affinity (KD) in pM | |
|---|---|---|---|
| | | mouse IL-1β | human IL-1β |
| Original Ig | 2H | 142 | 78.3 |
| Matured Ig | P2D7 | 10.9 | 3.1 |
| | P2D8 | 16.6 | 4.57 |
| | P1D9 | 23.6 | 6.73 |
| | P1H8 | 48.9 | 10.1 |

Sequences of Affinity Matured Clones

The matured clones were sequenced and the amino acid sequences of their light chain CDR3 region are presented in the Table 2.

TABLE 2

Amino acid sequences of the light chain CD3 region of each of the matured clones.

| | | |
|---|---|---|
| Original Ig | 2H | QAWDSNIEV (SEQ ID NO: 19) |
| Matured Ig | P1D9 | YAWDNAYEV (SEQ ID NO: 9) |
| | P1E8 | EAWDAAAEV (SEQ ID NO: 10) |
| | P1H8 | QAWADSFEV (SEQ ID NO: 11) |
| | P2D7 | YAWADTYEV (SEQ ID NO: 12) |
| | P2D8 | EAWADTYEV (SEQ ID NO: 13) |

The corresponding nucleotide sequences of the light chain CDR3 regions after reverse translation are presented below:

```
>2H (SEQ ID NO: 20)
CAGGCGTGGGACAGCAACATTGAAGTA     (original 2H
  A T        TTCT   T  C  G  T  sequence) (sequences
    A          A    A        C  encoding the same
    C          G             G  amino-acids)

>P1D9 (SEQ ID NO: 21)
TATGCTTGGGATAATGCTTATGAAGTT
  C  C       C  C  C  C G  C
     A          A     A    A
     G          G     G    G

>P1E8 (SEQ ID NO: 22)
GAAGCTTGGGATGCTGCTGCTGAAGTT
  G  C       C  C  C  C G  C
     A          A  A  A    A
     G          G  G  G    G

>P1H8 (SEQ ID NO: 23)
CAAGCTTGGGCTGATTCTTTTGAAGTT
  G  C       C CAGC   C  G  C
     A          A        A
     G          G        G

>P2D7 (SEQ ID NO: 24)
TATGCTTGGGCTGATACTTATGAAGTT
  C  C       C  C  C  C G  C
     A          A  A  A    A
     G          G  G  G    G

>P2D8 (SEQ ID NO: 25)
GAAGCTTGGGCTGATACTTATGAAGTT
  G  C       C  C  C  C G  C
     A          A  A  A    A
     G          G  G  G    G
```

Example 6—In Vivo Efficacy of P2D7KK

Derivation of P2D7KK

Out of the 5 affinity matured clones, P2D7 was selected and engineered to be a germline-like antibody, named P2D7KK. P2D7KK was derived from P2D7 by changing one arginine and one serine residues by lysine residues in positions 75 and 81 of the heavy chain variable region (FIG. 10).

P2D7KK was then tested for preliminary in vivo efficacy in 4 different animal models of disease (1) CAIA: collagen antibody-induced arthritis, a model of rheumatoid arthritis, (2) MSU: monosodium urate crystals-induced inflammation, a model mimicking gout, (3) RCC: renal cell carcinoma growth, to evaluate the use of IL-1β antibody in the tumour microenvironment to inhibit tumour growth and (4) *P. acnes*: a model of inflammatory acne using *Propionibacterium acnes*.

CAIA—Collagen Antibody-Induced Arthritis

Arthritis was induced in Balb/c mice by intraperitoneal injection of 1.5 mg/mouse of anti-collagen antibody cocktail at day 0, followed by injection of 25 pg of lipopolysaccharide (LPS) at day 3.

A group of 8 mice received 5 mg/kg of P2D7KK intraperitoneally at days 2, 5 and 9. Another group received 15 mg/kg of P2D7KK and one control group received 5 mg/kg of the isotype control following the same schedule.

Figure 11:
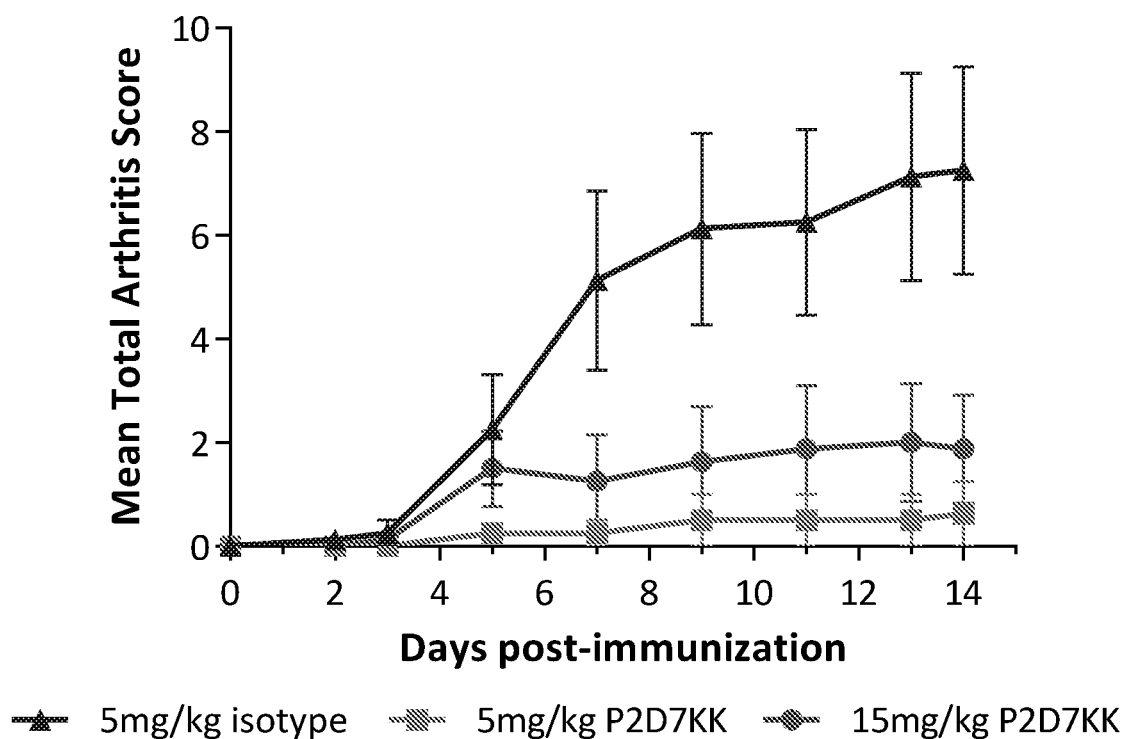
FIG. 11 shows arthritic scores in DBA mice after induction of arthritis with anti-collagen antibodies. Mice were injected either with 5 mg/kg isotype, 5 mg/kg P2D7KK or 15 mg/kg P2D7KK. The results show that mice treated with P2D7KK had much lower arthritic scores than mice injected with the isotype control.

The results showed that mice treated with P2D7KK have much lower arthritic scores than mice injected with the isotype control (FIG. 11). Accordingly, administration of P2D7KK inhibited the development of arthritis.

Figure 12:
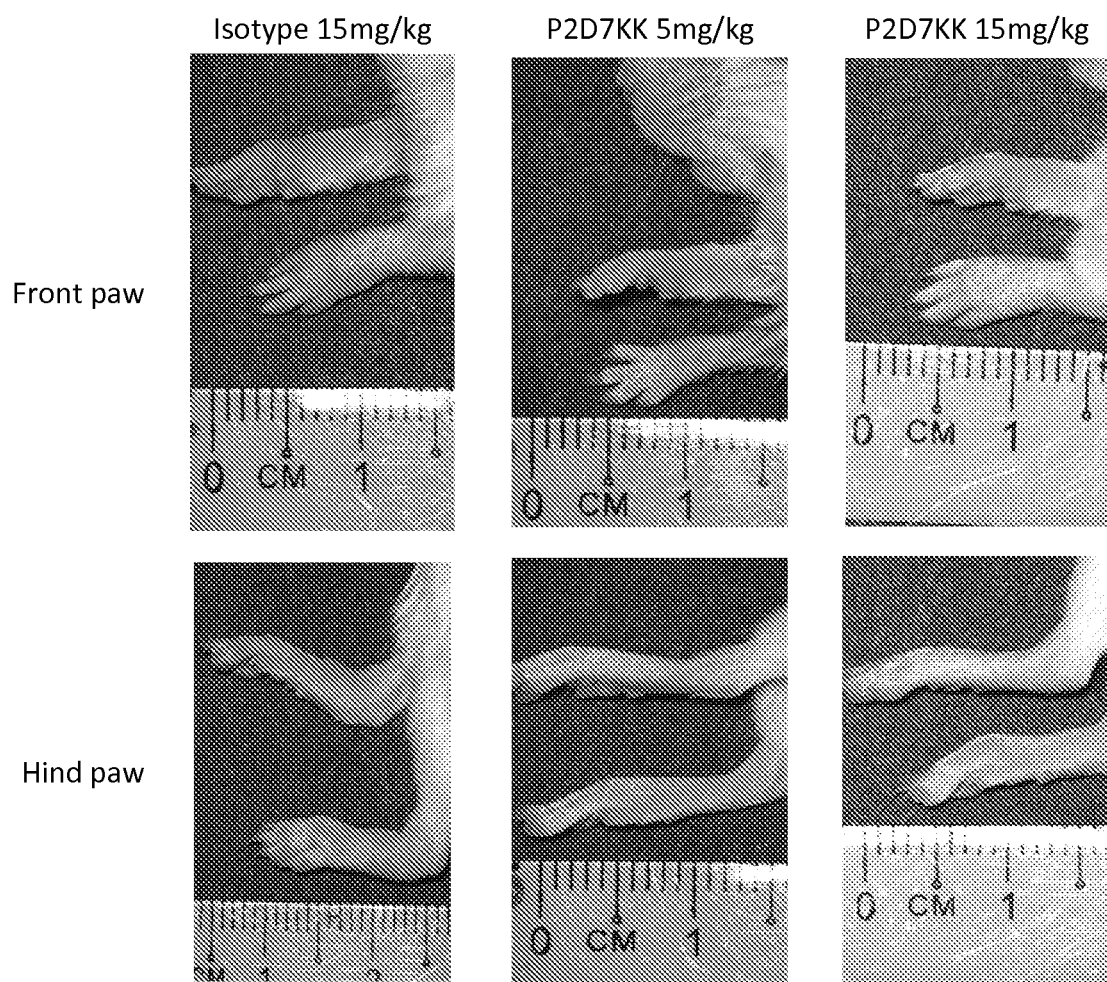
FIG. 12 shows a representative front (top) and hind (bottom) paw swelling after arthritis induction and administration of isotype control (left), P2D7KK 5 mg/kg (middle) or P2D7KK 15 mg/kg (right). The results show that P2D7KK clearly contained inflammation as mice treated with P2D7KK did not experience swelling of the paws as compared to mice injected with the isotype control.

The results also showed that P2D7KK clearly contained inflammation as mice treated with P2D7KK did not experience swelling of the paws as did the mice injected with an isotype antibody (FIG. 12).

Figure 13:
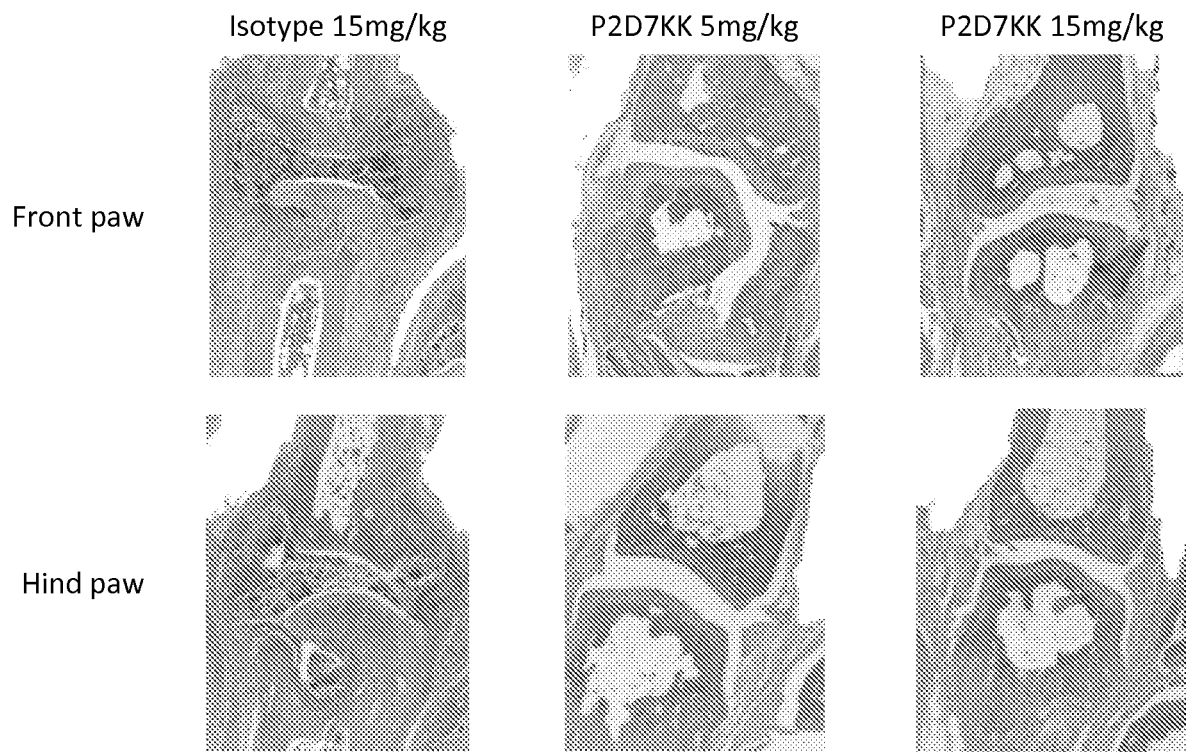
FIG. 13 shows a representative histological analysis of front (top) and hind (bottom) paws joints from mice injected with the isotype antibody (left) or treated with either 5 mg/kg (middle) or 15 mg/kg (right) of P2D7KK. The results show that in mice treated with P2D7KK, joints remain virtually free of immune cell infiltration while joints of isotype-injected mice were the site of a highly inflammatory reaction.

Histological analyses of hind paws showed that in mice treated with P2D7KK, joints remains virtually free of immune cells infiltration while joints of isotype-injected mice were the site of a highly inflammatory reaction (FIG. 13).

MSU—Monosodium Urate Crystals-Triggered Inflammation

Six groups of C57/BL6 mice were injected intraperitoneally with 3 mg of monosodium urate in 200 µL of PBS, or PBS alone for the control group. Mice were then injected with:

P2D7KK 5 mg/kg in 300 µL of PBS (n=5)
P2D7KK 15 mg/kg in 300 µL of PBS (n=4)
Isotype antibody 15 mg/kg in 300 µL of PBS (n=5)
Anakinra 30 mg/kg in 300 µL of PBS 9n=5)
300 µL of PBS (n=3, vehicle control group)
300 µL of PBS (n=5, no MSU control group)

Six hours after antibody administration, mice were culled and peritoneum lavaged with 5 mL of cold complete media. Neutrophils and monocytes were counted in lavage fluid by flow cytometry.

Figure 14:
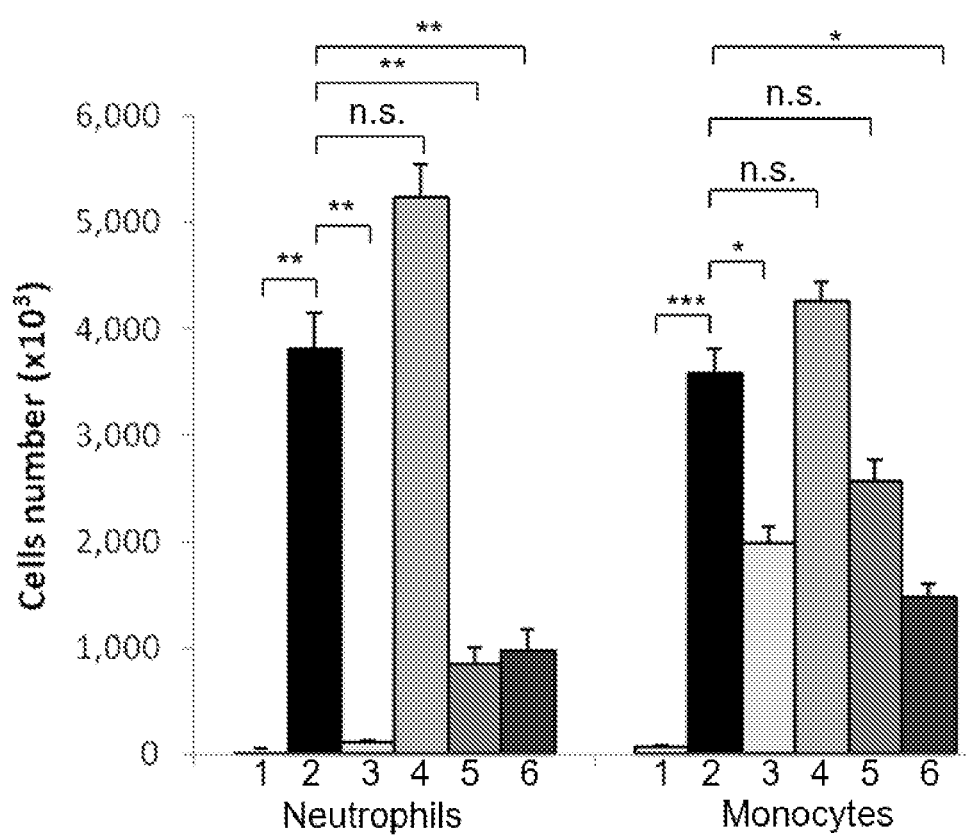
FIG. 14 shows infiltration of immune cells in the peritoneal cavity after injection of PBS (1) or monosodium urate crystals followed by administration of PBS (2), Anakinra 30 mg/kg (3), isotype human antibody 15 mg/kg (4), P2D7KK 5 mg/kg (5) or P2D7KK 15 mg/kg (6). Shown are mean±s.e.m. Unpaired t-test: *$p<0.05$; $p<0.01$; *$p<0.001$; n.s. not significant.

The results showed that injection of MSU in the peritoneum induces recruitment of neutrophils and monocytes. Like Anakinra, P2D7KK was able to significantly reduce infiltration of neutrophils (at both 15 and 5 mg/kg) and monocytes (only at 15 mg/kg) in the peritoneal cavity (FIG. 14).

RCC—Human Renal Cell Carcinoma Xenograft

Female SCID mice aged 6-8 weeks were injected intramuscularly with $2 \times 10^6$ RCC4 cells. One group of 6 mice then received 100 µg/mouse of P2D7KK injected in the tumour site, on days 1, 3, 5, 7 and 9 post-tumour inoculation. Another group of 6 mice received the isotype control antibody.

Tumour growth was monitored every 2 days between days 7 and 17.

Figure 15:
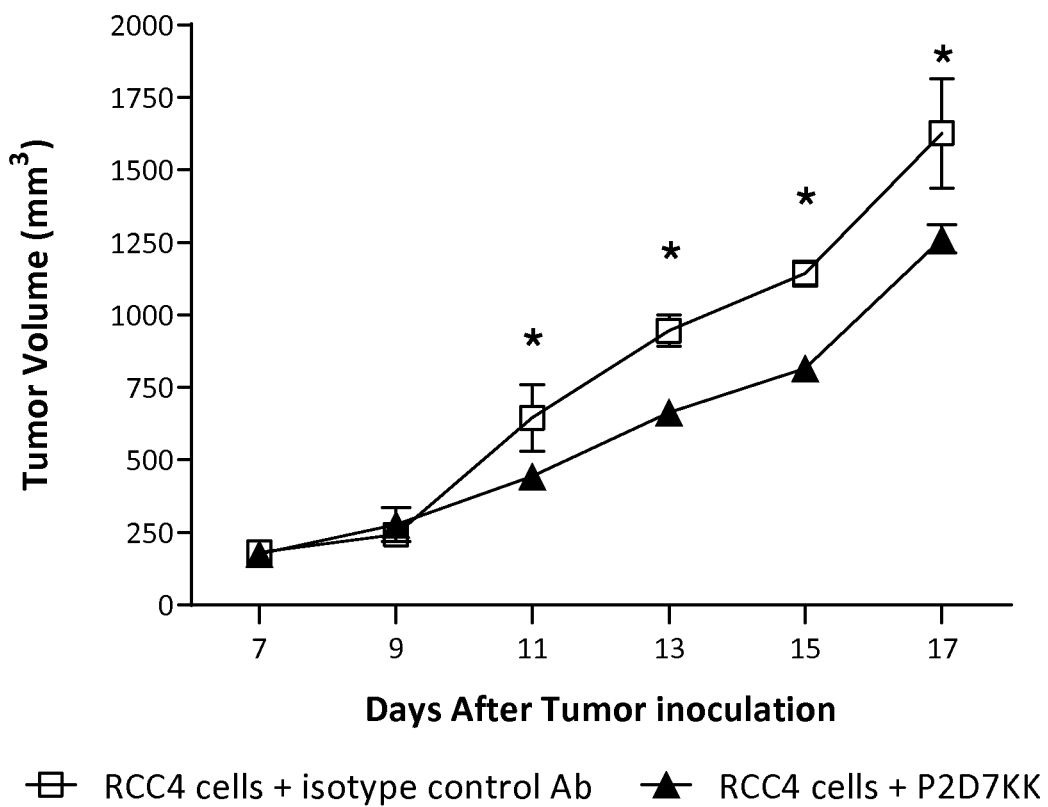
FIG. 15 shows tumour growth between days 7 and 17 post carcinoma cell inoculation in mice treated with P2D7KK or with the isotype control. Shown are means±SD, 2-way ANOVA test (Turkey's multiple comparison) *=$p<0.05$.

The results showed that P2D7KK significantly reduced tumour growth in the treated mice (FIG. 15).

*P. acnes*—Inflammatory Acne

C57/BL6 mice were injected intraperitoneally with 400 µg of either P2D7KK or the isotype control at day −1 and at day 1. At day 0, mice were infected with $10^8$ colony-forming units of *Propionibacterium acnes* in the right ear and received PBS in the left ear. Some control mice were not infected, some were infected but did not receive any antibody.

Immune parameters in the dermis and in the epidermis were assessed on days 2, 5 and 9.

Figure 16:
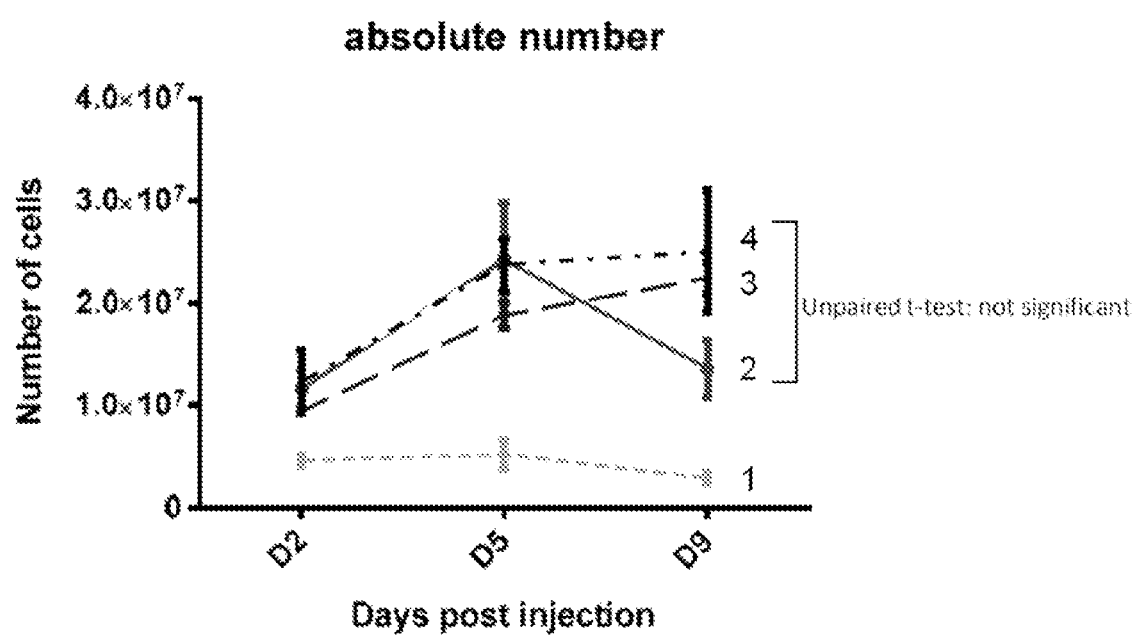
FIG. 16 shows absolute numbers of cells in mice auricular draining lymph nodes. Graph 1 represents mice not infected with *P. acnes*; graph 4 represents mice infected with *P. acnes* and injected with PBS; graph 3 represents mice infected with *P. acnes* and injected with isotype control; graph 2 represents mice infected with *P. acnes* and treated with P2D7KK.
Figure 17:
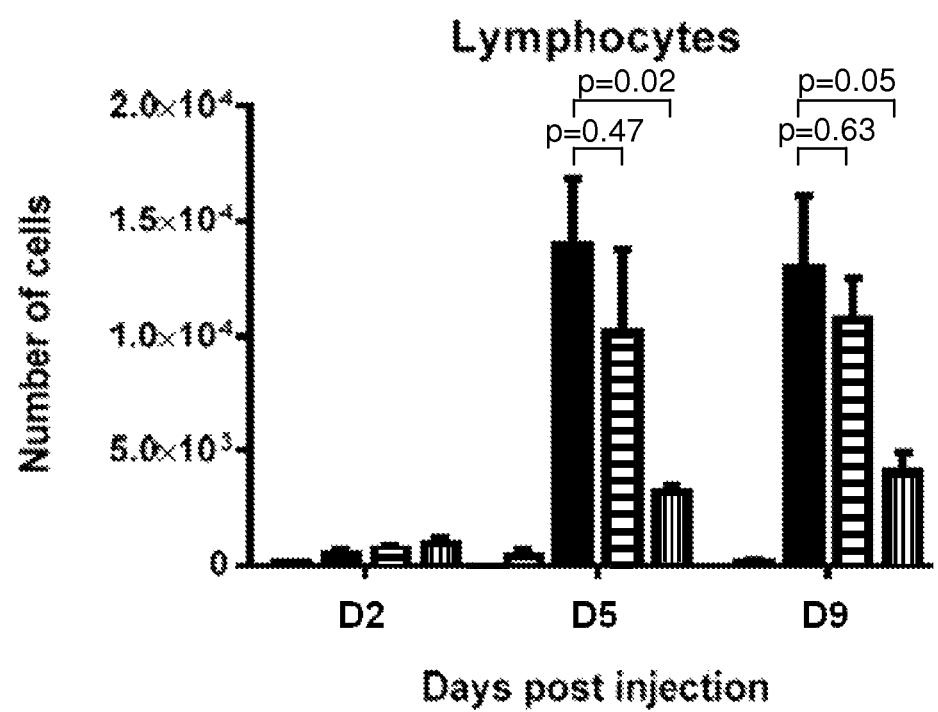
FIG. 17 shows the number of lymphocytes in epidermis of mice not infected with *P. acnes* (first bar from the left of each group), infected with *P. acnes* and injected with PBS (second bar from the left of each group), infected with *P. acnes* and injected with isotype control (third bar from the left of each group), or infected with *P. acnes* and treated with P2D7KK (fourth bar from the left of each group). p-values refer to an unpaired t-test.

The results showed that at day 9, P2D7KK reduced the inflammation as observed by the cell number decrease in the lymph nodes (FIG. 16). Without being bound by theory, it is likely that P2D7KK reduces lymphocytes infiltration in the epidermis (FIG. 17).

Accordingly, P2D7KK showed in vivo efficacy in 4 different models of human disease, namely rheumatoid arthritis, gout, renal cell carcinoma and inflammatory acne.

APPLICATIONS

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

---

The invention claimed is:

1. A method of inhibiting overexpression of IL-1β in a subject in need thereof, comprising administering to the subject an effective amount of an isolated monoclonal antibody which specifically binds to IL-1β, or an antigen binding fragment thereof, wherein said antibody or fragment thereof comprises:
   (i) Complementarity Determining Regions (CDRs) according to the Kabat numbering convention of a light chain comprising the amino acid sequence of SEQ ID NO: 17; and
   (ii) CDRs according to the Kabat numbering convention of a heavy chain comprising the amino acid sequence of SEQ ID NO: 14,
wherein the subject has an autoimmune disease.

2. The method of claim 1, wherein the IL-Iβ is human, and wherein the antibody or fragment is fully human.

3. The method of claim 2, wherein the antibody is of the subtype IgG1, IgG2, IgG3 or IgG4.

4. The method of claim 3, wherein the antibody is of the subtype IgG4.

5. The method of claim 1, wherein the antibody or fragment is in a composition, and wherein the composition further comprises a pharmaceutically acceptable carrier.

6. A method of inhibiting overexpression of IL-1β in a subject in need thereof, comprising administering to the subject an effective amount of an isolated monoclonal antibody which specifically binds to IL-1β, or an antigen binding fragment thereof, wherein said antibody or fragment thereof comprises the following Complementarity Determining Regions (CDRs):
   (i) a heavy chain variable region CDR H1 comprising the amino acid sequence set forth in SEQ ID NO: 26,
   (ii) heavy chain variable region CDR H2 comprising the amino acid sequence set forth in SEQ ID NO: 27,
   (iii) a heavy chain variable region CDR H3 comprising the amino acid sequence set forth in SEQ ID NO: 28,
   (iv) a light chain variable region CDR L1 comprising the amino acid sequence set forth in SEQ ID NO: 29,
   (v) a light chain variable region CDR L2 comprising the amino acid sequence set forth in SEQ ID NO: 30, and
   (vi) a light chain variable region CDR L3 comprising an amino acid sequence selected from the group consisting of: SEQ ID NO: 12, SEQ ID NO: 11, SEQ ID NO: 9, SEQ ID NO: 10, and SEQ ID NO: 13,
wherein the subject has an autoimmune disease.

7. The method of claim 6, wherein the light chain variable region CDR L3 comprises the amino acid sequence set forth in SEQ ID NO: 12.

8. The method of claim 6, wherein the light chain variable CDR3 comprises the amino acid sequence set forth in SEQ ID NO: 11.

9. The method of claim 6, wherein the IL-Iβ is human, and wherein the antibody or fragment is fully human.

10. The method of claim 6, wherein the antibody is of the subtype IgG1, IgG2, IgG3 or IgG4.

11. The method of claim 10, wherein the antibody is of the subtype IgG4.

12. The method of claim 6, wherein the antibody or fragment is in a composition, and wherein the composition further comprises a pharmaceutically acceptable carrier.

13. A method of inhibiting overexpression of IL-1β in a subject in need thereof, comprising administering to the subject an effective amount of an isolated monoclonal antibody which specifically binds to IL-1β, or an antigen binding fragment thereof, wherein said antibody or fragment thereof comprises:
   (i) a light chain sequence comprising the amino acid sequence of SEQ ID NO: 17; and
   (ii) a heavy chain sequence comprising the amino acid sequence of SEQ ID NO: 18, wherein the subject has an autoimmune disease.

14. The method of claim 13, wherein the heavy chain sequence comprises the amino acid sequence of SEQ ID NO: 14.

15. The method of claim 13, wherein the IL-Iβ is human, and wherein the antibody or fragment is fully human.

16. The method of claim 13, wherein the antibody is of the subtype IgG1, IgG2, IgG3 or IgG4.

17. The method of claim 16, wherein the antibody is of the subtype IgG4.

18. The method of claim 13, wherein the antibody or fragment is in a composition, and wherein the composition further comprises a pharmaceutically acceptable carrier.

* * * * *

SEQUENCE LISTING

```
<160> NUMBER OF SEQ ID NOS: 30

<210> SEQ ID NO 1
<211> LENGTH: 228
<212> TYPE: PRT
<213> ORGANISM: Homo sapiens

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Tyr Met His Trp Val Arg Gln Ala Pro Gly Gln Gly Leu Glu Trp Met
         35                  40                  45

Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Glu Trp Val Ala Gly Thr Glu Gly Trp Gly Tyr Tyr Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 2
<211> LENGTH: 222
<212> TYPE: PRT
<213> ORGANISM: Homo sapiens

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Arg Asn Gln Phe Ser Leu
 65                  70                  75                  80

Ser Leu Ser Ser Val Thr Ala Ala Asp Thr Ala Val Tyr Tyr Cys Ala
                 85                  90                  95

Arg Ala Ser Pro Ser Ser Gly Trp Thr Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
    210                 215                 220

<210> SEQ ID NO 3
<211> LENGTH: 218
<212> TYPE: PRT
<213> ORGANISM: Homo sapiens

<400> SEQUENCE: 3

Asn Phe Met Leu Thr Gln Pro His Ser Val Ser Glu Ser Pro Gly Lys
1               5                   10                  15

Thr Val Thr Ile Pro Cys Thr Ala Ser Ser Gly Ser Ile Ala Asn Asn
            20                  25                  30

Phe Val Gln Trp Tyr Gln Arg Pro Gly Ser Ala Pro Thr Thr Val
        35                  40                  45

Ile Tyr Glu Asp Ser Gln Arg Pro Ser Gly Val Pro Asp Arg Val Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ala Asn Asp Arg Val Thr Phe Gly Gly Gly Thr Lys Leu Ile Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Ala Glu Cys Ser
210                 215

<210> SEQ ID NO 4
<211> LENGTH: 212
<212> TYPE: PRT
<213> ORGANISM: Homo sapiens

<400> SEQUENCE: 4

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Phe Trp Tyr Gln Gln Lys Pro Gly Gln Ser Pro Val Leu Val Ile Tyr
        35                  40                  45

Leu Asp Asn Lys Arg Pro Ser Gly Ile Pro Glu Arg Phe Ser Gly Ser
50                  55                  60

```
Asn Ser Gly Asn Thr Ala Thr Leu Thr Ile Ser Gly Thr Gln Ala Leu
 65                  70                  75                  80

Asp Glu Ala Asp Tyr Tyr Cys Gln Ala Trp Asp Ser Asn Ile Glu Val
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 5
<211> LENGTH: 684
<212> TYPE: DNA
<213> ORGANISM: Homo sapiens

<400> SEQUENCE: 5

```
gaggtgcagc tggtacagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggactt gttgatcctg aagatggtga acaatatac      180 gcagagaagt tccagggcag agtcaccata accgcggaca cgtctacaga cacagcctac     240
atggagctga gcagcctgag atctgaggac acggccgtgt attactgtgc gagagttgag     300
tgggtggctg gtacggaagg ttgggggtac tactttgact actggggcca gggaaccctg     360
gtcaccgtct caagcgcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtccacac cttcccggct     540
gtcctacagt cctcaggact ctactccctc agcagcgtag tgaccgtgcc ctccagcagc     600
ttgggcaccc agacctacat ctgcaacgtg aatcacaagc ccagcaacac caaggtggac     660
aagaaagttg agcccaaatc ttgt                                            684
```

<210> SEQ ID NO 6
<211> LENGTH: 666
<212> TYPE: DNA
<213> ORGANISM: Homo sapiens

<400> SEQUENCE: 6

```
caggtgcagc tacagcagtg gggcgcagga ctgttgaagc cctcggagac cctgtccctc      60
acctgcgctg tctatggtgg gtccttcagt gattactact ggagctggat ccgccagccc     120
ccagggaagg ggctagagtg gattggggaa atcgatcata gtggaagcac caactacaac     180
ccgtccctca agagtcgagt caccatatca gtagacacgt ccaggaacca gttctccctg     240
```

```
agcctgagct ctgtgaccgc cgcggacacg gctgtttatt actgtgcgag agcgtccccg      300
agcagtggct ggacccttga ctactggggc cagggcaccc tggtcaccgt ctcaagcgcc      360
tccaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtccac accttcccgg ctgtcctaca gtcctcagga      540
ctctactccc tcagcagcgt agtgaccgtg ccctccagca gcttgggcac ccagacctac      600
atctgcaacg tgaatcacaa gcccagcaac accaaggtgg acaagaaagt tgagcccaaa      660
tcttgt                                                                 666

<210> SEQ ID NO 7
<211> LENGTH: 654
<212> TYPE: DNA
<213> ORGANISM: Homo sapiens

<400> SEQUENCE: 7
aattttatgc tgactcagcc ccactctgtg tcggagtctc cggggaagac ggtgaccatc       60
ccctgcaccg ccagcagtgg cagcattgcc aacaactttg tgcagtggta ccagcagcgc      120
ccgggcagtg cccccaccac tgtgatctat gaggatagtg aaagaccctc tggggtccct      180
gatcgggtct ctggctccat cgacagctcc tccaactctg cctccctcac catctctgga      240
ctgaagacta aggacgaggc tgattattac tgtcagtctt atgatagtgc aatgacaggg      300
gtgacattcg gcggagggac caagctgatc gtcctcggtc agcccaaggc tgccccctcg      360
gtcactctgt tcccgccctc ctctgaggag cttcaagcca acaaggccac actggtgtgt      420
ctcataagtg acttctaccc gggagccgtg acagtggcct ggaaggcaga tagcagcccc      480
gtcaaggcgg gagtggagac caccacaccc tccaaacaaa gcaacaacaa gtacgcggcc      540
agcagctatc tgagcctgac gcctgagcag tggaagtccc acagaagcta cagctgccag      600
gtcacgcatg aagggagcac cgtggagaag acagtggccc ctgcagaatg ctct            654

<210> SEQ ID NO 8
<211> LENGTH: 636
<212> TYPE: DNA
<213> ORGANISM: Homo sapiens

<400> SEQUENCE: 8
cagtctgtgt tgacgcagcc gccctcagtg tccgtgtccc caggacagac agccagcatc       60
acctgctctg gagataaatt gggggataaa tttgcttttct ggtatcagca gaagccaggc      120
cagtcccctg ttttggtcat ctatctagat aacaagcggc cctcagggat ccctgagcga      180
ttctctggct ccaactctgg gaacacagcc actctgacca tcagcgggac ccaggctttg      240
gatgaggctg actactactg tcaggcgtgg gacagcaaca ttgaagtatt cggcggaggg      300
accaagctga ccgtcctagg tcagcccaag gctgccccct cggtcactct gttcccgccc      360
tcctctgagg agcttcaagc caacaaggcc acactggtgt gtctcataag tgacttctac      420
ccgggagctg tgacagtggc ctggaaggca gatagcagcc ccgtcaaggc gggagtggag      480
accaccacac cctccaaaca aagcaacaac aagtacgcgg ccagcagcta cctgagcctg      540
acgcctgagc agtggaagtc ccacaaaagc tacagctgcc aggtcacgca tgaagggagc      600
accgtggaga gacagtggc ccctacagaa tgttca                                 636

<210> SEQ ID NO 9
<211> LENGTH: 9
```

```
<212> TYPE: PRT
<213> ORGANISM: Homo sapiens

<400> SEQUENCE: 9

Tyr Ala Trp Asp Asn Ala Tyr Glu Val
1               5

<210> SEQ ID NO 10
<211> LENGTH: 9
<212> TYPE: PRT
<213> ORGANISM: Homo sapiens

<400> SEQUENCE: 10

Glu Ala Trp Asp Ala Ala Ala Glu Val
1               5

<210> SEQ ID NO 11
<211> LENGTH: 9
<212> TYPE: PRT
<213> ORGANISM: Homo sapiens

<400> SEQUENCE: 11

Gln Ala Trp Ala Asp Ser Phe Glu Val
1               5

<210> SEQ ID NO 12
<211> LENGTH: 9
<212> TYPE: PRT
<213> ORGANISM: Homo sapiens

<400> SEQUENCE: 12

Tyr Ala Trp Ala Asp Thr Tyr Glu Val
1               5

<210> SEQ ID NO 13
<211> LENGTH: 9
<212> TYPE: PRT
<213> ORGANISM: Homo sapiens

<400> SEQUENCE: 13

Glu Ala Trp Ala Asp Thr Tyr Glu Val
1               5

<210> SEQ ID NO 14
<211> LENGTH: 222
<212> TYPE: PRT
<213> ORGANISM: Homo sapiens

<400> SEQUENCE: 14

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Ser Pro Ser Ser Gly Trp Thr Leu Asp Tyr Trp Gly Gln Gly
```

```
                100             105             110
Thr Leu Val Thr Val Ser Ser Ala Ser Thr Lys Gly Pro Ser Val Phe
            115             120             125
Pro Leu Ala Pro Ser Ser Lys Ser Thr Ser Gly Gly Thr Ala Ala Leu
            130             135             140
Gly Cys Leu Val Lys Asp Tyr Phe Pro Glu Pro Val Thr Val Ser Trp
145             150             155             160
Asn Ser Gly Ala Leu Thr Ser Gly Val His Thr Phe Pro Ala Val Leu
            165             170             175
Gln Ser Ser Gly Leu Tyr Ser Leu Ser Ser Val Val Thr Val Pro Ser
            180             185             190
Ser Ser Leu Gly Thr Gln Thr Tyr Ile Cys Asn Val Asn His Lys Pro
            195             200             205
Ser Asn Thr Lys Val Asp Lys Lys Val Glu Pro Lys Ser Cys
            210             215             220

<210> SEQ ID NO 15
<211> LENGTH: 212
<212> TYPE: PRT
<213> ORGANISM: Homo sapiens

<400> SEQUENCE: 15

Gln Ser Val Leu Thr Gln Pro Pro Ser Val Ser Val Ser Pro Gly Gln
1               5               10              15
Thr Ala Ser Ile Thr Cys Ser Gly Asp Lys Leu Gly Asp Lys Phe Val
            20              25              30
Tyr Trp Tyr Gln Gln Lys Pro Gly Gln Ser Pro Val Leu Val Ile Tyr
        35              40              45
Leu Asp Asn Lys Arg Pro Ser Gly Ile Pro Glu Arg Phe Ser Gly Ser
    50              55              60
Asn Ser Gly Asn Thr Ala Thr Leu Thr Ile Ser Gly Thr Gln Ala Leu
65              70              75              80
Asp Glu Ala Asp Tyr Tyr Cys Tyr Ala Trp Ala Asp Thr His Glu Val
            85              90              95
Phe Gly Gly Gly Thr Lys Leu Thr Val Leu Gly Gln Pro Lys Ala Ala
            100             105             110
Pro Ser Val Thr Leu Phe Pro Pro Ser Ser Glu Glu Leu Gln Ala Asn
            115             120             125
Lys Ala Thr Leu Val Cys Leu Ile Ser Asp Phe Tyr Pro Gly Ala Val
            130             135             140
Thr Val Ala Trp Lys Ala Asp Ser Ser Pro Val Lys Ala Gly Val Glu
145             150             155             160
Thr Thr Thr Pro Ser Lys Gln Ser Asn Asn Lys Tyr Ala Ala Ser Ser
            165             170             175
Tyr Leu Ser Leu Thr Pro Glu Gln Trp Lys Ser His Lys Ser Tyr Ser
            180             185             190
Cys Gln Val Thr His Glu Gly Ser Thr Val Glu Lys Thr Val Ala Pro
            195             200             205
Thr Glu Cys Ser
    210

<210> SEQ ID NO 16
<211> LENGTH: 212
<212> TYPE: PRT
<213> ORGANISM: Homo sapiens
```

<400> SEQUENCE: 16

Gln Ser Val Leu Thr Gln Pro Pro Ser Val Ser Val Ser Pro Gly Gln
1               5                   10                  15

Thr Ala Ser Ile Thr Cys Ser Gly Asp Lys Ile Arg Asp Lys Phe Val
            20                  25                  30

Phe Trp Tyr Gln Gln Lys Pro Gly Gln Ser Pro Val Leu Val Ile Tyr
        35                  40                  45

Leu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Tyr Ala Trp Ala Asp His Glu Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
            195                 200                 205

Thr Glu Cys Ser
        210

<210> SEQ ID NO 17
<211> LENGTH: 102
<212> TYPE: PRT
<213> ORGANISM: Homo sapiens

<400> SEQUENCE: 17

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Phe Trp Tyr Gln Gln Lys Pro Gly Gln Ser Pro Val Leu Val Ile Tyr
        35                  40                  45

Leu Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Tyr Ala Trp Ala Asp Thr Tyr Glu Val
                85                  90                  95

Phe Gly Gly Gly Thr Lys
            100

<210> SEQ ID NO 18
<211> LENGTH: 114
<212> TYPE: PRT
<213> ORGANISM: Artificial Sequence
<220> FEATURE:

<223> OTHER INFORMATION: Synthetic polypeptide

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Ser Pro Ser Ser Gly Trp Thr Leu Asp Tyr Trp Gly Gln Gly
            100                 105                 110

Thr Leu

<210> SEQ ID NO 19
<211> LENGTH: 9
<212> TYPE: PRT
<213> ORGANISM: Homo sapiens

<400> SEQUENCE: 19

Gln Ala Trp Asp Ser Asn Ile Glu Val
1               5

<210> SEQ ID NO 20
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 20
caggcgtggg acagcaacat tgaagta                                27

<210> SEQ ID NO 21
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 21
tatgcttggg ataatgctta tgaagtt                                27

<210> SEQ ID NO 22
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 22
gaagcttggg atgctgctgc tgaagtt                                27

<210> SEQ ID NO 23
<211> LENGTH: 27
<212> TYPE: DNA
<213> ORGANISM: Artificial Sequence -continued
<220> FEATURE:
<223> OTHER INFORMATION: Synthetic polynucleotide

<400> SEQUENCE: 23
caagcttggg ctgattcttt tgaagtt                                                27

<210> SEQ ID NO 24
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 24
tatgcttggg ctgatactta tgaagtt                                                27

<210> SEQ ID NO 25
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 25
gaagcttggg ctgatactta tgaagtt                                                27

<210> SEQ ID NO 26
<211> LENGTH: 5
<212> TYPE: PRT
<213> ORGANISM: Homo sapiens

<400> SEQUENCE: 26

Asp Tyr Tyr Trp Ser
1               5

<210> SEQ ID NO 27
<211> LENGTH: 16
<212> TYPE: PRT
<213> ORGANISM: Homo sapiens

<400> SEQUENCE: 27

Glu Ile Asp His Ser Gly Ser Thr Asn Tyr Asn Pro Ser Leu Lys Ser
1               5                   10                  15

<210> SEQ ID NO 28
<211> LENGTH: 11
<212> TYPE: PRT
<213> ORGANISM: Homo sapiens

<400> SEQUENCE: 28

Ala Ser Pro Ser Ser Gly Trp Thr Leu Asp Tyr
1               5                   10

<210> SEQ ID NO 29
<211> LENGTH: 10
<212> TYPE: PRT
<213> ORGANISM: Homo sapiens

<400> SEQUENCE: 29

Gly Asp Lys Leu Gly Asp Lys Phe Ala Phe
1               5                   10

<210> SEQ ID NO 30
<211> LENGTH: 7
<212> TYPE: PRT

```
<213> ORGANISM: Homo sapiens

<400> SEQUENCE: 30

Leu Asp Asn Lys Arg Pro Ser
1               5
```